(12) United States Patent
Burton

(10) Patent No.: US 7,531,646 B2
(45) Date of Patent: May 12, 2009

(54) β-D-RIBOSIDASE ACTIVITY INDICATORS WITH A CHROMOGENIC SUBSTRATE

(76) Inventor: Michael Burton, 14 Craven Court, Winwick Quay, Warrington, Chesire WA2 8QU (GB)

( * ) Notice: Subject to any disclaimer, the term of this patent is extended or adjusted under 35 U.S.C. 154(b) by 682 days.

(21) Appl. No.: 10/493,482

(22) PCT Filed: Oct. 24, 2002

(86) PCT No.: PCT/GB02/04799

§ 371 (c)(1),
(2), (4) Date: Apr. 23, 2004

(87) PCT Pub. No.: WO03/035900

PCT Pub. Date: May 1, 2003

(65) Prior Publication Data

US 2004/0235081 A1 Nov. 25, 2004

(30) Foreign Application Priority Data

Oct. 24, 2001 (GB) ................................. 0125532.2

(51) Int. Cl.
*A61K 31/351* (2006.01)
*A61K 31/7048* (2006.01)
*C07H 17/065* (2006.01)
*C07H 17/07* (2006.01)
*C07H 17/075* (2006.01)
*C07D 311/08* (2006.01)
*C07D 311/10* (2006.01)
*C07D 311/12* (2006.01)
*C07D 311/14* (2006.01)
*C07D 311/16* (2006.01)
*C07D 311/18* (2006.01)

(52) U.S. Cl. .............................. 536/8; 514/25; 514/457; 549/285; 549/289; 549/290; 549/403; 549/406

(58) Field of Classification Search ........................ None
See application file for complete search history.

(56) References Cited

FOREIGN PATENT DOCUMENTS

| EP | 0 567 026 | 10/1993 |
|---|---|---|
| EP | 0 710 725 | 5/1996 |
| FR | 2 770 538 | 11/1997 |
| NZ | WO97/31008 | * 8/1997 |
| WO | WO 00/48606 | 8/2000 |

OTHER PUBLICATIONS

James et al. (1997) Journal of Applied Microbiology, vol. 82, p. 532-536.*

Cornard et al. Mar. 1, 2001, Spectrochimica Acta Part A, vol. 57, p. 591-602.*
Day et al., "Conjugation Position of Quercetin Glucuronides and Effect on Biological Activity" Free Radical Biology and Medicine (2000) vol. 29 No. 12, pp. 1234-1243.*
Williams et al., "Correlations Between Leaf Flavonoids, Taxonomy and Plant Geography in the Genus Disporum" Phytochemistry (1993) vol. 34 No. 1, pp. 197-203.*
Hedin et al., "Isolation and Structural Determination of 13 flavonoid glycosides in hibiscus esculentus (okra)" American Journal of Botany (1968) vol. 44, No. 4, pp. 431-437.*
Reichel et al., "Chemistry and biochemistry of plant substances. XI. Synthesis of some new chalcone-flavanone-flavonol glucosides" Berichte der Deutschen Chemischen Gesellschaft [Abteilung] B: Abhandlungen (1943) vol. 76B pp. 1132-1134.*
Watanabe et al. "Synthesis and biological activity of 4,'8-dihydroxyisflavon -7-yl D-hexopyranosides" Carbohydrate Research pp. 283-289 dated Aug. 30, 2001.
Masao Shiozaki, "Synthesis of 4',8-dihydroxyisoflavon-7-yl D-arabinofuranoside" Exploratory Chemistry Research Laboratories pp. 1477-1482 dated 1999.
Tanaka et al. XP-002214142 Tannins and related Compounds XXI Isolation and Characterization of Galloyl and p-Hydroxybenzoyl Esters of Benzophenone and Xanthone C-Glucosides from Mangifera Indicia L. vol. 32 pp. 2676-2686 dated 1984.
James et al. XP002047085 " Evaluation of Cyclohexenoeculetin-B-D-Galactoside and 8-Hydroxyquinoline-B-D-Galactoside as Substrates for Detection of Galactosides" Applied and Enviromental Micribiology, vol. 62 No. 10 pp. 3868-3870, Dated 1996.
A. L. James et al. XP-000938196 "Alizarin-β-D-galactosides: a new substrate for the detection of bacterial β-galactosidase" The Society for pp. 336-Applied Microbiology, pp. 336-340 dated 2000.
Luukkhanen et al. XP-002214141 "Enzyme-Assisted Synthesis ansd Structural Characterization of Nitrocatechol Glucuronides" American Chemical Society, pp. 150-154 dated 1999.
Chaudry et al. XP-002214143 "Inhibition of human lens aidose redutase by flavonoids, sulindac idomethacin" Chemical Abstract vol. 99 No. 15 dated Oct. 10, 1983.

* cited by examiner

*Primary Examiner*—Shaojia Anna Jiang
*Assistant Examiner*—Eric S Olson
(74) *Attorney, Agent, or Firm*—Whitham Curtis Christofferson & Cook, P.C.

(57) ABSTRACT

This invention provides a method of detecting enzyme activity on a solid medium. The enzyme substrate has a chromogenic portion comprising a catechol residue, in which a derivitising moiety is linked to the aromatic ring of the catechol via a bond, and an enzyme cleavable group which is attached via an ester or ether linkage to the oxygen atom derived from a hydroxyl group of the catechol residue. If the enzyme substrate contacts an enzyme capable of cleaving the enzyme cleavable groups and the cleaved compound contacts a chelatable metal ion, a substantially non-diffusable coloured precipitate is formed.

7 Claims, No Drawings

β-D-RIBOSIDASE ACTIVITY INDICATORS WITH A CHROMOGENIC SUBSTRATE

This application is a national stage application of PCT/GB02/04799, filed Oct. 24, 2002, which claims priority to foreign application GB0125532.2, filed Oct. 24, 2001.

FIELD

This invention relates to enzyme substrates which are used to detect enzyme activity.

PRIOR ART

A wide variety of enzyme substrates have been described that show utility for detecting microbial and/or enzyme activity (S. F. Dealler, Reviews in Medical Microbiology, 1993, 4, 198-206). These substrates may be either natural substances (e.g. esculin and indoxyl sulfate) or synthetic molecules (e.g. 4-methylumbelliferyl-β-D-galactopyranoside, 4-nitrophenyl-β-D-glucuronide). These substrates contain moieties that are either fluorogenic or chromogenic (or become so after development with another reagent) and another portion, such as a carbohydrate, organic acid (usually as an ester), inorganic acid (typically a phosphate or sulfate ester) or amino acid, which may be cleaved by specific enzymes in the systems under investigation. The cleavage of the substrate results in the release of the fluorogenic or chromogenic portion. This cleaved portion, either on its own or after treatment with a developing agent(s), produces fluorescence or colour and thus can demonstrate the presence of the specific enzyme activity. In suitably designed test systems this activity can be used to identify and enumerate micro-organisms.

One of the most widely used series of fluorogenic enzyme substrates is based on 4-methylumbelliferone (the 4MU-substrates). For instance, 4-methylumbelliferyl-β-D-glucuronide (MUG) has found extensive use in microbiological media for the detection of β-glucuronidase (GUS) positive strains of E. coli (M. Manafi et al., Microbiological Reviews, 1991, 55, 335-348). However, despite its high sensitivity, this and other 4MU-substrates suffer from several disadvantages. One disadvantage is that the intensity of fluorescence is pH dependant. Another major limitation of these substrates on plated microbiological media is that the released 4-methylumbelliferone diffuses widely in the commonly used agar-based systems and this makes it difficult to pick out positive colonies from within a mixed culture. Other common fluorescent labels include resorffin and fluorescein. These substrates also have disadvantages including spreading. Another problem is the difficulty of preparing them in an adequately pure form on an industrial scale. All fluorogenic labels are limited by the need to utilize UV incident light to detect their presence.

Chromogenic substrates based on p- and o-nitrophenol (PNP- and ONP-substrates respectively) are also very well established indicators for specific enzyme activities. The yellow nitrophenolate generated on cleavage is very suitable for liquid media but, as with the fluorescent 4MU-substrates, the intensity of the colour is pH dependent and diffusion on agar media is considerable (M. Manafi, Int. J. Food Microbiol., 1996, 31, 45-58).

5-Bromo-4-chloro-3-indolyl β-galactopyranoside (X-gal) is one of the commonest substrates and is used to demonstrate β-galactosidase for several purposes, for instance in cloning studies involving the LacZ+ gene and in the detection of various coliform bacteria. Enzymatic cleavage of this substrate will initially produce 5-bromo-4-chloroindoxyl. Although this is not chromogenic itself, it may react with another molecule of released 5-bromo4-chloroindoxyl via an oxidative process to form an insoluble blue-green indigoid-type dye (S. Cotson and S. J. Holt, Proc. Roy. Soc. B, 1958, 148, 506-519). Employed in agar based media, X-gal positive microbial strains appear as easily visible blue-green colonies with minimal diffusion of the dye into the surrounding media. The substrate 5-bromo-4-chloro-3-indolyl-α-galactopyranoside (X-α-gal) is used to detect α-galactosidase activity in gene expression studies with yeast.

The indoxylic chromophore can be modified to produce more red or amethyst shades by the introduction of a halogen atom into the 6-position of the indole ring. In this way 6-chloro-3-indolyl-derived substrates can be used as alternatives to the X-substrates. Moreover, when different carbohydrates or other enzymatically cleavable molecules are attached to the X- and 6-chloro-3-indolyl groups respectively, it has been possible to produce microbiological media which both demonstrate and differentiate between at least two separate micro-organisms in a mixture (J. N. Roth and W. J. Ferguson, U.S. Pat. No. 5,210,022 [1993]; D. G. Flowers and M. Sternfeld, U.S. Pat. No. 5,364,767 [1994]). However, the different types of indoxyl-substrate have different rates of hydrolysis and oxidation. As a consequence 6-chloro-3-indolyl substrates produce weakly coloured colonies and there is also more diffusion into the surrounding medium when compared with the corresponding X-substrate. Another disadvantage of the indoxyl-substrates is that because the coloured dye is generated under oxidative conditions they are not suitable for the detection of microbes that require strictly anaerobic conditions for growth.

Other classes of substrate rely on the ability of a molecule liberated upon cleavage to form an insoluble coloured chelate in the presence of a suitable metal ion. One such compound is 8-hydroxyquinoline (8HQ). 8HQ-β-D-glucoside has been used to identify β-glucosidase activity (A. L. James et al, Zentralbl. Bakteriol. Mikrobiol., 1987, Ser A 267, 188-193), but toxicity problems have been encountered (A. Albert at al, Br. J. Exp. Pathol., 1953, 34, 119-130). Another compound of this nature is esculetin (6,7-dihydroxy-2H-1-benzopyran-2-one) (1).

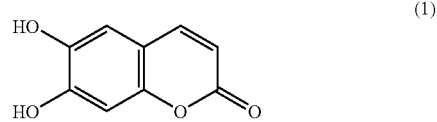

(1)

Esculin (esculetin-6-β-D-glucopyranoside) is a widely used probe for the detection of β-glucosidase activity in microbial systems (e.g. Listera identification). When used in a solid medium in conjunction with inter alia a suitable iron salt, the liberated esculetin forms a chelate which gives rise to highly visible brown colonies for β-glucosidase positive strains. However there is still some diffusion in the media. The problem of diffusion was only overcome (A. L. James, et al, J. Appl. Microbiol., 1997, 82, 532-536; A. L. James and L. Armstrong, WO 97/41138) by the synthesis of novel esculetin derivatives in which the bicyclic system had been substituted in the 3 and/or 4 positions. The lead example reported had been elaborated into a tricyclic system, namely the 3,4-cyclohexentesculetin (CHE) (2).

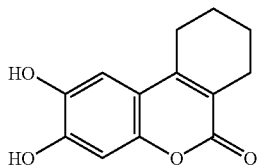

(2)

When utilised in an iron-containing solid medium, CHE-substrates yield intense black chelates. However the optimal concentration required to demonstrate enzyme activity is more than three times that required with an X-substrate. CHE-Gal has also been described by James et al in App. Env. Microbiol. (1996) 62(10), 3868-3870.

Another example in which an insoluble coloured chelate can be formed from a cis-dihydroxytricyclic system has been found by the use of alizarin β-D- galactopyranoside (3) (A. L. James et al., *Lettr, Appl. Microbiol.*, 2000, 30, 336-340).

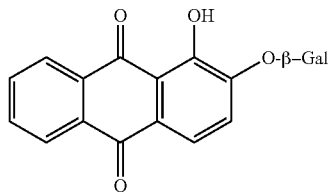

(3)

Upon hydrolysis by bacterial enzymes, this substrate generated bright-violet or bright-red colonies in the presence of iron and aluminium salts respectively. The colonies were also highly localised on Columbia agar plates. The concentration needed for visualisation was less than one-fifth that required for CHE-gal.

Before the current invention was made a cis-dihydroxybicyclic system, such as that in esculetin, could be utilised as the basis for a chelating type of enzyme substrate, but problems with diffusion could only be overcome by elaboration of this system via substitution or by extension to a tricyclic system such as that present in CHE and alizarin.

Before the current invention was developed simple 1,2-dihydroxybenzenes like catechol and its derivatives (4) had received scant attention as enzyme substrates.

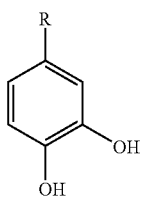

(4)

Glycosides of catechol (4, R═H) have been reported to be cleaved to a varying degree by enzymes (B. Helferich et al., *J prakt. Chem.*, 1933, 138, 275-280; K. Bock and S. Refn, *Acta Chem. Scand.*, 1989, 43, 373-380). Catechol is colourless and therefore the progress of the enzymatic hydrolysis had been conveniently monitored by spectrophotometric analysis or by measuring the quantity of carbohydrate released. The anion of 4-nitrocatechol (4, R═NO2) is yellow and this compound, as a monosulfate salt (5) had been used as a chromogenic substrate in a manner analogous to p-nitrophenyl sulphate (W. D. Bostick et al. *Clin. Chem.*, 1978, 24, 1305-1316; A. L. Fluharty et al., *Biochem. Biophys. Res. Comm.*, 1974, 59, 455-461). In addition, the ability of this compound to reduce cupric ferricyanide to cupric ferrocyanide (known as Hatchett's brown) enabled it to be employed to detect arylsulfatase activity by this means (J. S. Hanker et al., *Histochemistry*, 1975, 41, 207-225). Other phenolic compounds not possessing a cis-1,2-dihydroxy system can also be utilised for the production of Hatcheft's brown.

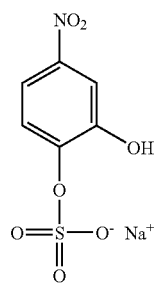

(5)

Luukkanen, L., et al, in Bioconjugate Chem. (1999)10, 150-154 describe the enzyme-assisted synthesis of a series of nitrocatechol O-glucuronides. The glycosides are believed to be hydrolysed by microsomal β-glucuronidase and possibly also by *E. coli* β-glucuronidase in the intestine. Luukkanen et al do not disclose any hydrolysis tests. Indeed, they attempt to inhibit hydrolysis by including an inhibitor in the enzyme containing synthesis medium. Nor do the authors indicate whether the glycosides or a glycones are coloured.

Shiozaki, M. in Tetrahedron:Asymmetry (1999) 10, 1477-1482 and Watanabe, Y., et al in Carbohydrate Res. (2001) 335, 283-289 describe the synthesis and properties of 4',8-dihydroxy-isoflavon-7-yl-α-D-arabinoside (A-76202) and four hexopyranoside analogues. The glycosides are linked to the 7 position, i.e. to the ring which is fused. The glycosides are said to be inhibitors of α-glucosidase, an enzyme of the endoplasmic reticulum. Enzyme activity and inhibition was determined by-the use of 4-nitrophenyl-α-D-glucopyranoside, a chromogenic enzyme substrate for the enzyme, in a liquid phase reaction system.

WO-A-0048606 describes phosphate derivatives of phenolic compounds, including catechol derivatives based on 1,2-dihydroxy benzene, used as prodrugs. Although the catechol may be a flavonoid, no examples of flavonoids are disclosed.

Many glycosides of flavonoids are naturally occurring compounds and/or have been synthesised. 3,3',4'-Trihydroxyflavone-4'-β-D-glucopyranoside and 3',4'-dihydroxyflavone-4'-β-D-glucopyranoside, for instance, are known compounds. Many such compounds have been used as glycosidase enzyme substrates. For instance, in Lambert, N., et al (1999) Biochim. Biophys. Acta 1435, 110-116 glucosides of various flavonoids are used to investigate the activity of a cytosolic β-glucosidase from pig liver. The cleavage is carried out in a liquid medium and the products are identified by HPLC. Further flavonoid and isoflavonoid glucosides are used as substrates for cell-free extracts from human small intestine and liver containing different glucosidase enzymes in Day, A. J., et al (1998) FEBS Letters 436, 71-75. The reactions are carried out in liquid media and products are, again, analysed by HPLC.

SUMMARY OF THE INVENTION

This invention provides a method of detecting enzyme activity on a solid medium including:
a) contacting an enzyme substrate, comprising
   i) a chromogenic portion comprising a catechol residue and
   ii) an enzyme cleavable group which is attached via an ester or ether linkage to the oxygen atom derived from a hydroxyl group of the catechol residue
   with a substance suspected of containing an enzyme capable of cleaving the enzyme cleavable group, to produce a cleaved compound
b) contacting the cleaved compound, optionally after intermediate reactions, with a metal ion which is chelatable by the cleaved compound, or the product of any intermediate steps, to produce a substantially non-diffusible coloured precipitate that is visible in the presence of the substrate and the metal ion; and
c) detecting the presence of the non-diffusible precipitate.

A catechol residue, for the present specification is a moiety resulting from removal of one or both hydroxylic hydrogen atoms from a 1,2-dihydroxybenzene or a substituted derivative thereof, preferably substituted with a derivatising moiety which is linked to the aromatic ring of the catechol via a bond. In the substrate one or both of the hydroxylic oxygen atoms of the residue is used to link to an enzyme cleavable group. The aromatic ring may be unsubstituted or substituted with one or more derivatizing moieties, provided that the substituents do not form a ring system fused to the 1,2-dihydroxy benzene ring.

A cleaved compound is the chromogenic portion of the substrate after enzyme action has removed the enzyme cleavable groups. The precipitated chelate should be visible in the presence of the substrate and the-metal ion, so that its presence may be detected visually. The substrate and metal ion may together (e.g. as a chelate) or separately be coloured provided that the colour is different to that of the said precipitated chelate.

A wide variety of enzyme cleavable groups may be used in the enzyme substrates of this invention. Examples of the types of bonds formed between the catecholic hydroxyls and the enzyme deavable groups include ester linkages when the catecholic hydroxyl is linked to an acyl group eg derived from an amino acid or fatty acid, and phosphate, sulphonate or sulfate ester linkages when the enzyme cleavable groups are phosphatyl, sulphonyl or sulphatyl respectively. When the enzyme cleavable group is a sugar moiety joined via an ether linkage, this forms as part of the cyclic acetal structure. When the enzyme deavable group is a sugar residue, the sugar may be α or β linked to the catechol residue and may be the L or D form of the sugar unless otherwise stated. Generally the oxygen atom which is retained when the enzyme cleavable group and the catecholic hydroxyl are linked was originally part of the catechol.

In an enzyme detection system such as envisaged by the current invention it is possible to control the status of this reaction by adding the enzyme substrate when required and then later adding the chelatable metal ion. This may have advantages under certain situations. It is, however, preferred that the method described above will take place with the chelatable metal ion present during step (a). This will enable the cleaved chromogenic portion to chelate the metal ion as it is produced thereby preventing any diffusion of the cleaved compound which may occur if the cleaved compound in its non-chelated state is diffusable.

The chelatable metal ion mentioned in step (b) of the method may be any metal ion which the cleaved compound can chelate. When the metal ion is present in the solid medium or during step (a) of the method the metal ion should be one which is tolerated by any target micro-organisms growing on the media. It will be seen that a wide range of chelatable metal ion compounds may be used within this invention. Especially preferred chelatable metal ion compounds are iron salts aluminium salts and bismuth salts.

The substantially non-diffusible coloured precipitates formed in this invention are formed by chelation of a chelatable metal ion by the cleaved compound and mean that the site of enzyme activity is detected by distinct site specific colouration. The presence of the non-diffusable precipitate is used as a direct indication of the presence of the enzyme activity to be detected.

The advantage that the coloured precipitate of step (c) is detectable by eye, and preferably using visible incident light, means that the result of tests may be determined quickly by the naked eye, without the need for other equipment such as a UV lamp or a spectrophotometer and the overall detection method is simpler.

A glycoside (6) of catechol itself was produced and tested with respect to its ability to generate an insoluble chelate in the presence of an iron salt and the appropriate glycosidase-producing micro-organisms.

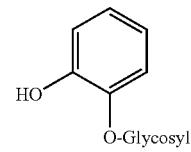

(6)

It was found that this compound produced a purple-coloured chelate that was approximately equivalent to esculetin in respect of both colour intensity and the extent of diffusion on an agar plate. However, the diffusion is quite considerable and catechol is inferior to CHE in this respect. Nonetheless it had been demonstrated that the cis- or 1,2-dihydroxy system does not need to be part of a fused bicyclic or tricyclic system such as is the case with esculetin, CHE or alizarin to produce a useful chelating type of enzyme substrate. Catechol is cheaper than esculetin, and therefore used in this manner catechol-substrates like (6) could provide more readily available alternatives to esculin or other esculetin based substrates.

The preferred enzyme substrates in the above method are those wherein the catechol residue has a derivatising group attached to the aromatic ring, preferably meta or, more preferably para to the atom substituted by the enzyme cleavable group. It is most-preferred that the derivatising group comprises at least 4 atoms. It is particularly preferred that the substituent is aryl, heteroaryl, cycloheteryl or cycloalkyl. In one class of the preferred enzyme substrates the catechol residue comprises a dihydroxyflavonoid, dihydroxyaurone or dihydroxychalcone structure. Some examples of catechol residues from which the chromogenic portions are formed (by replacement of one of the hydroxylic hydrogen atoms by a cleavable group) are given below. In structures 8 to 13 the catechol is a dihydroxyflavonoid, in structure 14 it is a dihydroxyaurone and in structure 15 it is a dihydroxychalcone and in 16 is a flavanol. This invention may also employ natural glycosides of-other members of the flavonoid series such as spiraeoside wherein the chromogenic portion has a quercetin based structure (17).

In the structures the core ring structure is indicated with the two hydroxyl groups at the 3' and 4' position which are essential in the derivatisable compounds. The names are the core compounds without the 3' and 4' hydroxyl groups. A particularly preferred residue is based on 3',4'-dihydroxyflavone or its 3'-lower alkoxy derivative. Quercetin already possesses the 3' and 4' hydroxyl groups unlike the other structures indicated.

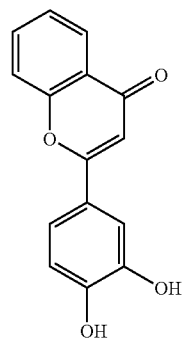
Flavone (8)
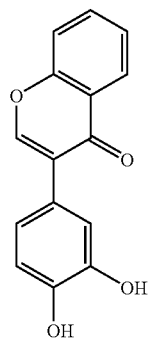
Isoflavone (9)
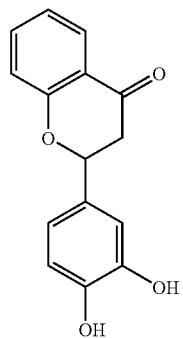
Flavanone (10)
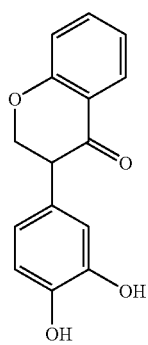
Isoflavanone (11)
-continued
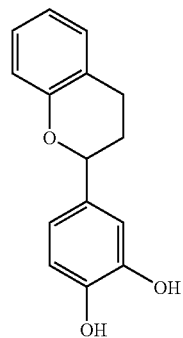
Flavan (12)
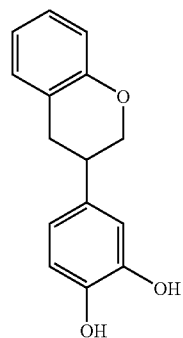
Isoflavan (13)
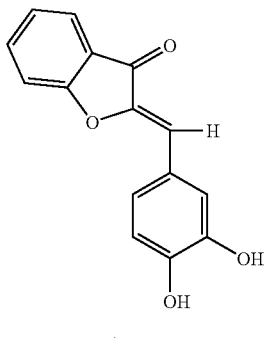
Aurone (14)
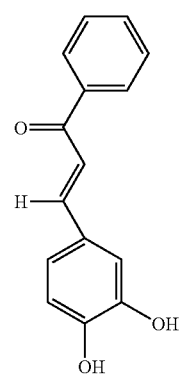
Chalcone (15)

-continued

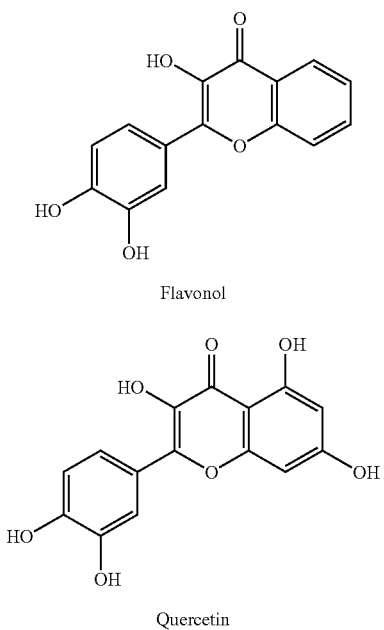

(16) Flavonol

(17) Quercetin

The enzyme substrates of use in the method of this invention may also be described according to the following structural formulae:

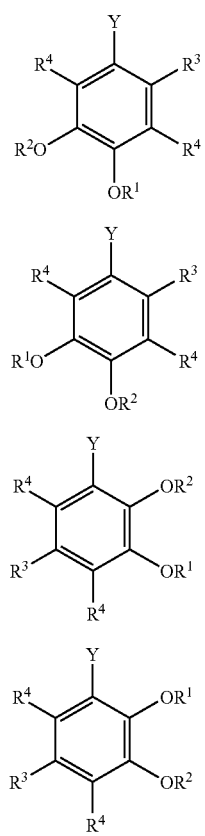

I

II

III

IV wherein $R^1$ and $R^2$ are H or any enzymically cleavable group and $R^1$ and $R^2$ cannot both be H.

Y, $R^3$ and $R^4$ are moieties which do not interfere with enzyme cleavage or chelate formation.

The compounds of the formulae I, II, III and IV may have one enzyme cleavable group which may be positioned at $R^1$ or at $R^2$. Alternatively these compounds may have two enzymically cleavable groups which are positioned at $R^1$ and $R^2$.

The compounds of this invention may be fully derivatised wherein Y, $R^3$ and $R^4$ are organic moieties containing less than 40 atoms, preferably less than 30 atoms and more preferably less than 20 atoms. In another embodiment the compounds of this invention may only be partially derivatised wherein $R^4$ is H. In yet another embodiment the compounds of this invention may have only one derivatising moiety which is attached to the catechol ring wherein $R^3$ and $R^4$ are H, in such embodiments it is preferred that Y contains four or more atoms. In another class of compounds Y is acyl, for instance COPhe, where Phe is phenyl or —CHO.

Y may comprise substituted or unsubstituted aryl or heteroaryl groups containing 5 to 18 ring atoms. In some embodiments Y may contain only one ring group such as

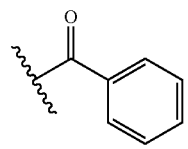

Y preferably has a core structure of V or VI,

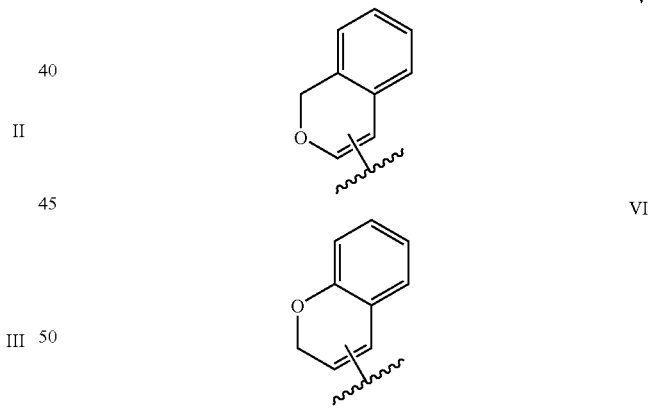

V

VI wherein the structures are linked to the catechol ring as shown.

"Core structure" means the skeleton of Y which may further be substituted. Examples of substituents are hydroxyl, $C_{1-24}$ alkyl, $C_{2-12}$ alkenyl, $C_{1-4}$ alkoxy, acyl including —CHO and COPhe where Phe is phenyl, =O, halogen, nitro, aryl and acyloxy groups. Alkyl and aryl groups which are substituents may be substituted by amino, hydroxyl, peptide, acyloxy, alkoxy and aryl groups. The bond terminating with a zig zag is joined to the rest of the molecule,. i.e. the catechol ring.

Preferably $R^1$ is an enzyme cleavable group. Preferably Y is para to $OR^1$, that is the compound is of the formula I.

It is preferred that Y has the structure of VI or VIII

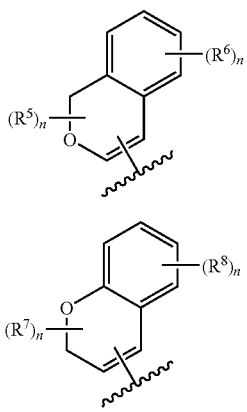

VII

VIII wherein each of $(R^5)_n$, $(R^6)_n$, $(R^7)_n$ and $(R^8)_n$ may represent more than one substituent and would include =O. $R^5$, $R^6$, $R^7$ and $R^8$ are substituents which do not interfere with enzyme action or metal ion chelation, preferably selected from the group consisting of hydroxyl, $C_{1-24}$ alkyl, $C_{2-12}$ alkenyl, $C_{1-4}$ alkoxy, acyl including —CHO and COPhe where Phe is phenyl, =O, halogen, nitro, aryl and acyloxy groups. Alkyl and aryl groups which are substituents may be substituted by amino, hydroxyl, peptide, acyloxy, alkoxy and aryl groups or two group $R^6$ and $R^8$ on the same carbon are =O.

The most preferred embodiments of Y are represented by structures IX and X

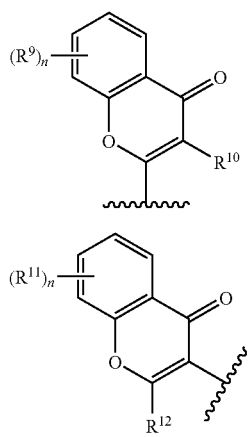

IX

X wherein $(R^9)_n$ and $(R^{11})_n$ represent one or more substituents and $R^{10}$ and $R^{12}$ are each hydrogen or a substituent, any or all of which substituents do not interfere with the enzyme cleavage or metal ion chelation. $R^9$, $R^{10}$, $R^{11}$ and $R^{12}$ are preferably selected from the group consisting of hydroxyl, $C_{1-24}$ alkyl, $C_{2-12}$ alkenyl, $C_{1-4}$ alkoxy, acyl including —CHO and COPhe where Phe is phenyl, =O, halogen, nitro, aryl and acyloxy groups. Alkyl and aryl groups which are substituents may be substituted by amino, hydroxyl, peptide, acyloxy, alkoxy and aryl groups. Most preferably Y is IX, and $R^{10}$ is hydrogen, hydroxyl, $C_{1-4}$ alkoxy or $OR^x$ where $R^x$ is an enzyme cleavable as group.

In embodiments where $(R^6)_n$, $(R^8)_n$, $(R^9)_n$ and $(R^{11})_n$ represent more than one substituent including =O the double bonds in the substituted ring are rearranged. Preferably n is 0, 1 or 2.

$R^3$ and $R^4$ may be selected from the group consisting of H, $C_1$ to $C_6$-alkyl, -alkoxy and hydroxyalkyl, halogeno, nitro, acyl, acyloxy, aralkyl, aryl and amido groups. $R^3$ and $R^4$ are not linked to form a fused ring.

For the method of this invention to work only one of $R^1$ and $R^2$ needs to be substituted by an enzymically cleavable group. In this way, upon enzyme cleavage and liberation of the enzyme cleavable group, the adjacent hydroxyl groups necessary for chelation of the chelatable metal ion are exposed and the substantially non-diffusable coloured precipitate can form. In a different embodiment both $R^1$ and $R^2$ may be substituted by an enzymically cleavable group. These enzymically cleavable groups can optionally be identical or different. If these groups are identical then one type of enzyme activity is, necessary to cause cleavage and production of the substantially non-diffusable coloured precipitate. If $R^1$ and $R^2$ represent different enzymically cleavable groups then two enzyme activities are required before the substantially non-diffusable coloured precipitate is formed. This may be useful in instances where the target microbe or enzyme extract of interest contains two enzyme activities and the commensal microbes or other enzyme extracts contain only one of these enzyme activities.

The methods of the present invention rely upon enzyme action to remove the enzyme cleavable group or groups to reveal adjacent (i.e. cis) hydroxy groups in the cleaved compound.

Molecules not preferable in forming the catechol residue of the current invention are those which have a pair of adjacent hydroxyl groups elsewhere on the skeleton i.e. two adjacent hydroxyls as $R^6$, $R^8$, $R^9$ or $R^{10}$; possession of these groups may result in the chelate being formed in the absence of enzymatic hydrolysis thus causing darkening of the plated media. Other molecules not preferable have a group which is non-enzyme cleavable such as —$CH_3$ at either $R^1$ or $R^2$.

A general scheme for the synthesis of a substrate composed of a sugar residue and a catechol residue connected via an ether linkage involves a sugar with protected hydroxyl groups being mixed together with catechol or a catechol derivative and a catalyst to form the catechol (derivative) glycoside. Optionally further derivatising moieties may be added to the catechol residue. The sugar moiety is deprotected and the chromogenic enzyme substrate is purified. A general scheme for producing chromogenic enzyme substrates comprising a catechol residue and a phosphoryl linked via a phosphate ester bond may involve reacting the catechol derivative and one molar equivalent of phosphorous oxychloride or other phosphorylating agent mixed in an aprotic solvent. After the reaction is complete the substrate may be purified.

When the substance suspected of containing enzyme activity comprises microbes the method of the invention may comprise a preliminary method step of growing the microbes on a solid medium. In such an embodiment where the substrate is present in the medium during the microbial growth, the presence of enzyme activity is detected by strongly coloured microbial colonies. The colouration remains substantially within the colony and does not diffuse into or across the solid, usually agar, medium.

The method of this invention may be used with anaerobic bacteria which are grown on the solid medium under anaerobic conditions. This may be useful in situations where gut bacterial studies or studies on other anaerobic bacteria such as soil bacteria, for example *Clostridia*, are necessary. In such a situation it may be preferred that the enzyme cleavable groups are phosphates.

For ease of carrying out the method of this invention it is envisaged that the chromogenic enzyme substrate and the chelatable metal ion are present in a solid medium which supports the growth of microbes. It will be understood that the microbes which can be studied using the method of this invention can be fungal, bacteria or viral although they are most preferably bacteria.

The method of this invention may be carried out with the enzyme substrates of the currently described method as the only detection system. The person skilled in the art will also appreciate that the solid medium may contain one or more additional selection or detection systems. Non-limiting examples for additional selection or detection systems are antibiotics, enzyme substrates, chromogenic or fluorogenic indicators, enzyme inducers, growth factors and growth inhibitors as appropriate for the required test procedure.

The person skilled in the art will also appreciate that the enzyme cleavable groups of the compounds of this method may be any group which is cleavable by the enzyme activity which is required to be detected. Therefore a non-limiting list of possibilities would include residues of phosphates, sulphates, amino acids, sugars, fatty acid groups, proteins, nucleotides and peptides. Preferred embodiments have glycosyls as the enzyme cleavable groups.

A further aspect of this invention provides novel compounds comprising i) a chromogenic portion comprising a catechol residue, and ii) an enzyme cleavable group which is attached via an ester or ether linkage to the oxygen atom derived from a hydroxyl group of the catechol residue and the enzyme cleavable groups are selected from fucosyl, ribosyl, arabinosyl, mannosyl, xylosyl, α- or β-linked glucosyl, β-linked glucuronyl, α- or β-galactosyl, phosphatyl, and acyl groups.

The compounds of one class of the invention have a β-D-ribofuranosyl group as the enzyme cleavable group. Other preferred embodiments have phosphatyl, α- or β-galactosyl, α- or β-glucosyl, myo-inositolphosphatyl, octanoyl or decanoyl groups.

When the enzyme cleavable groups are sugar residues they may be attached via either α or β linkages and either the L or D sugar may be used unless otherwise stated.

The novel compounds of this invention may be produced as the hydrate or in the form of a suitable salt.

It is generally expected that compounds of this invention which have one or more derivatising moieties, will have at least one of the derivatising moieties attached to the catechol ring para to an enzyme cleavable group.

In the following description when the novel compounds are based on a flavanoid structure the following numbering system is used

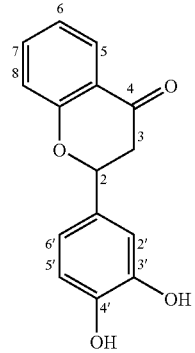

The novel compounds form a preferred embodiment when at least one of the enzyme cleavable groups is β-D-ribofuranosyl. Still further preferred compounds are selected from catechol-β-D-ribofuranoside, 3',4'-dihydroxyflavone-4'-β-D-ribofuranoside, 3,4-dihydroxybenzaldehyde-4-β-D-ribofuranoside, 3,4-dihydroxychalcone-4-β-D-ribofuranoside, 4-nitrocatechol-1-β-D-ribofuranoside, 3',4'-dihydroxyaurone-4'-β-D-ribofuranoside, 3,4-dihydroxybenzaldehydesemicarbazone-4-β-D-ribofuranoside, 3,3',4'-trihydroxy-flavone-4'-β-D-ribofuranoside, 3',4'-dihydroxy-3-methoxyflavone-4'-β-D-ribofuranoside and their derivatives. These compounds are claimed in applicants co-pending PCT application claiming priority from GB 0125528.0.

Especially preferred embodiments of novel compounds include enzyme substrates of structural formula I wherein $R^2$, $R^3$ and $R^4$ are H and Y takes structural formula IX wherein $R^{10}$ is H, there are no substituents $R^9$ (n=0) and $R^1$ is selected from the list given below. Alternatively described the enzyme substrate comprises a chromogenic residue formed from a catechol residue which is 3',4'-dihydroxyflavone and an enzyme cleavable group which is attached via an ester or ether linkage to the oxygen atom derived from a hydroxyl group of the catechol residue. The enzyme cleavable groups, or $R^1$ are selected from 4'-β-D-glucuronyl, 4'-β-D-galactopyranosyl, 4'-α-D-galactopyranosyl, 4'-decanoyl, 4'-octanoyl, 4'-inositol-1-phosphatyl, 4'-phosphatyl, 4'-β-ribofuranosyl, 4'-α-L-arabinopyranosyl, 4'-butyryl, 4'-nonanoyl, 4'-palmitoyl, 4'-lignoceroyl, 4'-α-L-fucopyranosyl, 4'-β-L-fucopyranosyl, 4'-α-D-fucopyranosyl, 4'-β-D-fucopyranosyl, 4'-α-D-mannopyranosyl, 4'-β-D-mannopyranosyl, 4'-oleoyl, 4'-sulphatyl, 4'-α-D-xylopyranosyl and 4'-β-D-xylopyranosyl and derivatives of these enzyme cleavable groups.

A second group of especially preferred embodiments of novel compounds include enzyme substrates of structural formula I wherein $R^2$, $R^3$ and $R^4$ are H and Y takes structural formula IX wherein $R^{10}$ is —OH and there are no substituents $R^9$ and $R^1$ is selected from the list given above and 4'-α-D glucopyranosyl and derivatives of these enzyme cleavable groups. Alternatively described the enzyme substrate comprises a chromogenic residue formed from a catechol residue which is 3,3',4'-trihydroxyflavone and an enzyme cleavable group which is attached via an ester or ether linkage to the oxygen atom derived from a hydroxyl grup of the catechol residue. The enzyme cleavable groups or $R^1$ are selected from the list given above and 4-α-D-glucyopyranosyl and derivatives of these enzyme cleavable groups.

A third group of especially preferred embodiments of novel compounds include enzyme substrates of structural formula I wherein $R^2$, $R^3$ and $R^4$ are H, $R^1$ is selected from the list given below and Y takes structural formula IX wherein $R^{10}$ is a $C_{1-6}$ alkoxy group and there are no substituents $R^9$. Alternatively described the enzyme substrate comprises a chromogenic residue formed from a catechol residue which is 3',4'-dihydroxy-3-$C_{1-6}$ alkoxyflavone. A fourth group of preferred embodiments includes enzyme substrates of structural formula I wherein $R^2$, $R^3$ and $R^4$ are H and Y takes structural formula IX wherein $R^{10}$ is —OCH$_3$ and there are two $R^9$ substituents, —OH and —OCH$_3$ substituted at positions 5 and 7 respectively. Alternatively described the enzyme substrate comprises a chromogenic residue formed from a catechol residue which is 3,7-dimethyl-quercetin. For both the third and fourth groups the enzyme cleavable group or $R^1$ can be selected from the list given for the second group of novel enzyme substrates and 4'-β-D-glucopyranoside and derivatives of these enzyme cleavable groups.

A further aspect of this invention provides a kit of components for use in the detection of enzyme activity on a solid medium which includes an enzyme substrate, comprising
  i) a chromogenic portion comprising a catechol residue, and
  ii) an enzyme cleavable group which is attached via an ester or ether linkage to the oxygen atom derived from a hydroxyl group of the catechol residue and
    a compound of a metal ion which is chelated by the cleaved chromogenic portion.

In this aspect of the invention the metal ion is, for instance, selected from the group consisting of $Zn^{2+}$, $Co^{2+}$, $Mn^{2+}$, $Cu^{2+}$, $Sn^{2+}$, $Ba^{2+}$, $Al^{3+}$, $Sr^{2+}$, $Bi^{2+}$ and $Fe^{3+}$. $Zn^{2+}$ and $Co^{2+}$ are less preferred as their presence may inhibit growth of some interesting microbes. $Fe^{3+}$, $Al^{3+}$ and $Bi^{2+}$ are particularly suitable.

The enzyme substrate of the kit may be further defined as described above.

A skilled person will understand that such a kit of components will have a wide range of uses. Therefore such kits will have the components optionally ready mixed or in separate containers. When the components are presented ready mixed this provides ease of use. When the components are in separate containers the user may determine the optimal proportions for the detection procedure to be carried out.

When the substance suspected of containing enzyme activity comprises microbes which are to be grown on a solid medium, a solid medium which supports the growth of microbes which comprises the kit components listed above will be used. In a corresponding embodiment of the kits described above the kit comprises the constituents of the solid medium which supports the growth of microbes and comprises the components of the kits described above. Such a kit may have its constituents in a non-hydrated form which are optionally ready mixed or in separate containers.

This invention will now be further illustrated by way of examples.

EXAMPLE 1

Synthesis and Evaluation of 3',4'-dihydroxyflavone-4'-β-D-glucopyranoside sodium salt (DHF-glucoside)

A 50 ml round bottomed flask provided with a stopper and a magnetic stirrer was charged with 3 Å molecular sieves (3.7 g), 3',4'-dihydroxyflavone (DHF) (750 mg), dichloromethane (20 ml) and then this mixture was stirred for 5 minutes. Thereafter was added β-D-glucose pentaacetate (1.0 g) and the mixture was stirred for a further 10 minutes before the addition in one portion of boron trifluoride diethyl etherate (3.0 ml). After stirring for one hour the reaction mixture was filtered and the filtrate transferred to a separating funnel where it was washed five times with an equal volume of saturated sodium bicarbonate solution. After separation the organic layer was dried over magnesium sulfate for 16 hours before removal of the drying agent and evaporation to afford the glycoside tetraacetate as an amber foam (480 mg). The glycoside tetraacetate (100 mg) was suspended in methanol (0.2 ml) and a solution containing sodium (10 mg) in methanol (0.1 ml) was added in one lot. On agitation a yellow precipitate formed. Upon leaving to stand at ambient temperature for 16 hours, diethyl ether (3 ml) was added to the mixture and the solid was harvested by filtration. After washing with diethyl ether (4 ml) in four portions the solid was immediately transferred to a desiccator and dried under vacuum over phosphorous pentoxide for 2 hours. The product took the form of a bright yellow powder (30 mg).

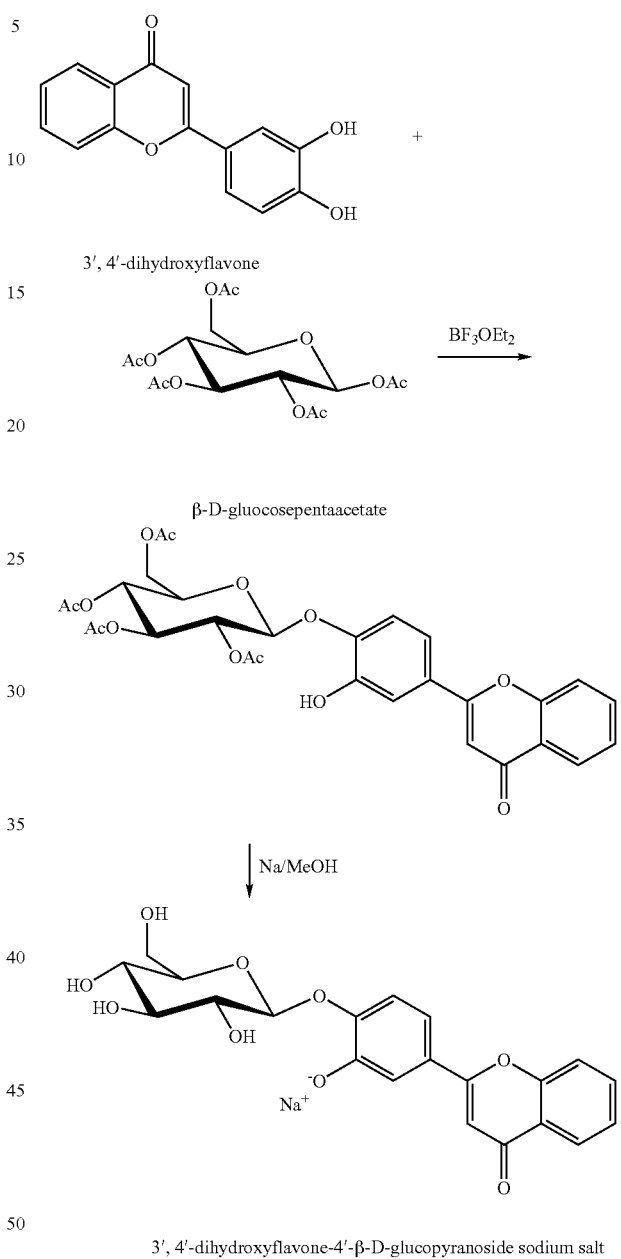

3', 4'-dihydroxyflavone-4'-β-D-glucopyranoside sodium salt

Evaluation Method

The glucoside derivative of DHF was tested with 194 distinct strains of bacteria. The choice of bacteria included a wide range many of which are important pathogens or commensals commonly isolated from pathological samples.

The substrate was added to Columbia agar at a substrate concentration of 300 mg/l. Ferric ammonium citrate was included at 500 mg/l. All ingredients were autoclaved at 116° C. for 20 minutes to ensure sterilisation. Agar plates were then prepared in 90 mm petri dishes. The substrates caused a yellow colouration of the agar.

For each strain tested, a bacterial suspension was prepared in sterile deionised water at an inoculum of approximately $1.5 \times 10^8$ colony forming units per ml. This was achieved using a densitometer. 1 μl of each bacterial suspension was then inoculated onto each plate using a multipoint inoculator. Strains were inoculated in parallel onto Columbia agar containing ferric ammonium citrate with no substrate (negative control).

After 18 hours incubation strains were examined visually for the presence of colour. Any strains producing a black colouration on substrate-containing media but not on the negative control plates were deemed to be hydrolysing the substrate.

Results

Of 120 Gram negative bacteria tested, 20% hydrolysed DHF-glucoside. The strains which were 'positive' generally produced a brown/black colouration which showed no diffusion in agar. The positive strains were generally expected to be positive based on previous findings using indoxylic substrates. There were 11 strains, known to be producers of β-glucosidase, which did not appear to hydrolyse DHF-glucoside. These strains have been previously shown to be reactive with analogous substrates such as X-glucoside and CHE-glucoside. If DHF-glucoside is to be used to specifically detect glucosidase producing Gram-negative bacteria then this would be an obvious weakness in its performance. The results are shown in Table 1 below.

In diagnostic microbiology chromogenic glucosides are generally employed to detect Gram positive bacteria and are commonly employed, for example, for the detection of enterococci and listeria. Of 74 Gram positive bacteria tested 22.5% hydrolysed DHF-glucoside. Those Gram-positive bacteria tested here which were known to be glucosidase producers all showed excellent activity with DHF-glucoside. Strains of Listeria and enterococci produced intense black colonies with no diffusion of the black chelate. DHF-glucoside shows excellent potential for the detection of these strains and compares favourably with CHE-glucoside in this respect. The results are shown in Table 2 below.

EXAMPLE 2

Synthesis and Evaluation of 3',4'-dihydroxyflavone-4'-β-D-ribofuranoside Sodium Salt (DHF-riboside)

A 50 ml round bottomed flask equipped with a stopper and a magnetic stirrer was charged with 3',4'-dihydroxyflavone (Lancaster Synthesis Ltd, Lancashire, UK) (500 mg), β-D-ribofuranose tetraacetate (640 mg), 3 Å molecular sieves (5.2 g) and dichloromethane (20 ml). The mixture was stirred for 15 minutes, then the boron trifluoride diethyl etherate catalyst (20 ml) was added in one portion. Stirring was continued for a further 20 minutes, then the reaction mixture was poured into a solution of saturated sodium bicarbonate (150 ml). The organic layer was diluted by the addition of more dichloromethane (30 ml) and then separated from the yellow aqueous layer in a separating funnel. The organic layer was then washed eleven times with an equal volume of saturated sodium bicarbonate solution then dried for one hour over magnesium sulfate. After removal of the drying agent, evaporation of the dichloromethane yielded the glycoside triacetate as a dark gum (390 mg). To this gum (315 mg) was added a sodium methoxide solution that had been made by dissolving sodium (50 mg) in methanol (5 ml). After agitating for a few minutes the gum dissolved and the solution was left at ambient temperature for 16 hours. The solution was then concentrated to a volume of approximately 2 ml by evaporation after which addition of diethyl ether (10 ml) caused the product to precipitate. It was collected by vacuum filtration and, after washing with diethyl ether (20 ml) in four portions was immediately transferred to a desiccator and dried over phosphorous pentoxide under vacuum for 2 hours. The product obtained was a yellow powder (201 mg).

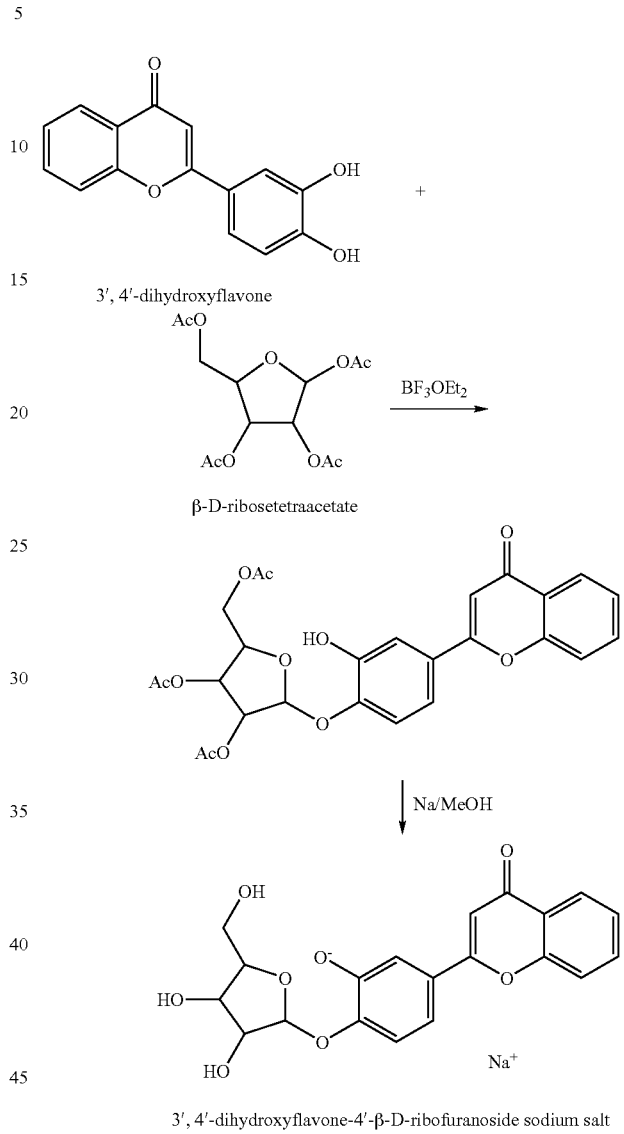

Evaluation Method

The same method was used as in Example 1.

Results

Of 120 Gram negative bacteria tested 68.3% hydrolysed DHF-riboside. Those which were positive produced a clearly visible black chelate which remained restricted to bacterial colonies without diffusion into the surrounding agar. Detection of activity capable of cleaving the β-D-ribofuranosyl group (herein called β-ribofuranosidase) allowed for distinctions to be made between closely related genera or species. Most of the Enterobacteriaceae tested were strongly positive for β-ribofuranosidase activity. An exception was Yersinia enterocolitica, a pathogen which is a cause of enteritis. This substrate could have a useful role for differentiation of this species from closely related bacteria. The fact that the Shigella genus was uniformly positive for ribofuranosidase activity was also notable. None of the glycosidases commonly sought in diagnostic microbiology are uniformly produced by species of *Shigella* and this is a limiting factor in designing methods for their detection. This may allow for distinction between *Shigella* and closely related species such as *Proteus*.

A further point of interest among the activities of Gram-negative bacteria concerns the *Vibdonaceae*. Culture media for the detection of *Vibrio* species do not allow for the differentiation of *Aeromonas* species which is commonly found in the environment and is very closely related to *Vibrio*. Most of the *Vibrio* species tested here, including the two main pathogens *V. cholerae* and *V. parahaemolyticus*, do not express β-ribofuranosidase. This is in contrast to *Aeromonas* species which are highly active. This may allow for a simple means of differentiating between these two closely related species. The results of these tests are shown in Table 1.

Among the Gram-positive bacteria tested only 30.8% were active with this substrate. All of the *staphylococci* were positive but there was no differentiation between the different species of *staphylococci* tested. *Streptococci* were almost universally negative whereas enterococci ('faecal streptococci') were variable in their activity. The main point of interest was that *Corynebacterium diphtheriae* and *Arcanobacterium haemolyticum* were active with this substrate. Both of these species are found in the throat of infected humans and throat cultures are therefore performed to isolate and identify these pathogens. The aerobic commensal flora of the throat is dominated by *streptococci* and DHF-riboside may provide a means of differentiating these two pathogens from the normal commensal flora of the throat. The results of these tests are shown in Table 2.

TABLE 1

Hydrolysis of glycosides of 3'4'-dihydroxyflavone by Gram negative bacteria.

| Strain | Reference No. | β-Glucoside | β-Riboside |
|---|---|---|---|
| *E. coli* 0157 | NCTC 12079 | – | ++ |
| *E. coli* 0157 | NCTC 12080 | – | ++ |
| *E. coli* 0157 | NCTC 12900 | – | ++ |
| *E. coli* 0157 | NCTC 13125 | – | ++ |
| *E. coli* 0157 | NCTC 13126 | – | ++ |
| *E. coli* 0157 | NCTC 13127 | – | ++ |
| *E. coli* 0157 | NCTC 13128 | – | ++ |
| *E. coli* | NCTC 10418 | – | ++ |
| *E. coli* | ECO 2 | – | ++ |
| *E. coli* | ECO 3 | – | ++ |
| *E. coli* | ECO 4 | – | ++ |
| *E. coli* | ECO 5 | – | ++ |
| *E. coli* | ECO 6 | – | ++ |
| *E. coli* | ECO 7 | – | ++ |
| *E. coli* | ECO 8 | – | ++ |
| *E. coli* | ECO 9 | – | ++ |
| *E. coli* | ECO 10 | – | ++ |
| *E. coli* | ECO 11 | – | ++ |
| *E. coli* | ECO 12 | – | ++ |
| *Shigella boydii* | NCTC 9327 | – | ++ |
| *Shigella boydii* | NCTC 9732 | – | ++ |
| *Shigella boydii* | NCTC 9850 | – | ++ |
| *Shigella dysenteriae* (type 4) | NCTC 9759 | – | ++ |
| *Shigella dysenteriae* (type 2) | NCTC 9952 | – | ++ |
| *Shigella dysenteriae* (type 3) | NCTC 9720 | – | ++ |
| *Shigella flexneri* | NCTC 8192 | – | ++ |
| *Shigella flexneri* | NCTC 9723 | – | ++ |
| *Shigella flexneri* | NCTC 9780 | – | ++ |
| *Shigella sonnei* | NCTC 9774 | – | ++ |
| *Shigella sonnei* | NCTC 8574 | – | ++ |
| *Shigella sonnei* | NCTC 10352 | – | ++ |
| *Shigella sonnei* | NCTC 8219 | – | ++ |
| *Shigella sonnei* | NCTC 8586 | – | ++ |
| *Hafnia alvei* | NCTC 8105 | – | ++ |

TABLE 1-continued

Hydrolysis of glycosides of 3'4'-dihydroxyflavone by Gram negative bacteria.

| Strain | Reference No. | β-Glucoside | β-Riboside |
|---|---|---|---|
| *Hafnia alvei* | HAL 2 | – | ++ |
| *K. pneumoniae* | NCTC 10896 | –* | ++ |
| *K. pneumoniae* | KPN 2 | –* | ++ |
| *K. pneumoniae* | KPN 3 | –* | ++ |
| *K. pneumoniae* | KPN 4 | –* | ++ |
| *K. oxytoca* | KOX 1 | + | ++ |
| *K. oxytoca* | KOX 2 | + | ++ |
| *C. freundii* | NCTC 9750 | + | ++ |
| *C. freundii* | CFR 1 | + | ++ |
| *C. freundii* | CFR 2 | – | ++ |
| *C. freundii* | CFR 3 | – | ++ |
| *C. freundii* | CFR 4 | + | ++ |
| *C. diversus* | CDI 1 | – | ++ |
| *C. diversus* | CDI 2 | – | ++ |
| *Serratia marcescens* | NCTC 10211 | + | ++ |
| *Serratia* spp. | SEX 1 | + | ++ |
| *Serratia* spp. | SEX 2 | + | ++ |
| *Serratia* spp. | SEX 3 | –* | ++ |
| *Serratia* spp. | SEX 4 | –* | ++ |
| *Aeromonas hydrophila* | NCTC 8049 | ++ | ++ |
| *Aeromonas caviae* | NCTC 10852 | ++ | ++ |
| *Aeromonas sobria* | NCTC 11215 | – | 0 |
| *E. cloacae* | NCTC 11936 | –* | ++ |
| *E. cloacae* | ECL 1 | –* | ++ |
| *E. cloacae* | ECL 2 | –* | ++ |
| *E. cloacae* | ECL 3 | –* | ++ |
| *E. cloacae* | ECL 4 | –* | ++ |
| *E. aerogenes* | NCIMB 10102 | + | ++ |
| *E. aerogenes* | EAE 1 | + | ++ |
| *Salmonella typhimurium* | NCTC 74 | – | ++ |
| *Salmonella typhi* | NCTC 8385 | – | ++ |
| *Salmonella motevideo* | SAX 55 | – | ++ |
| *Salmonella oranienburg* | SAX 56 | – | ++ |
| *Salmonella hadar* | SAX 57 | – | ++ |
| *Salmonella panama* | SAX 58 | – | ++ |
| *Salmonella orthmarchen* | SAX 59 | – | ++ |
| *Salmonella alachia* | SAX 60 | – | ++ |
| *Y. enterocolitica* | NCTC 11176 | – | – |
| *Y. enterocolitica* | NCTC 11177 | – | – |
| *Y. enterocolitica* | NCTC 11600 | – | – |
| *Y. enterocolitica* | NCTC 10460 | – | – |
| *A. lwoffii* | ATCC 15309 | – | – |
| *A. baumanii* | ATCC 19606 | – | – |
| *A. calcoaceticus* | ATCC 7844 | – | – |
| *P. aeruginosa* | NCTC 10662 | – | + |
| *P. aeruginosa* | ATCC 10145 | – | + |
| *M. morganii* | NCTC 235 | – | – |
| *M. morganii* | MMO 1 | + | + |
| *M. morganii* | MMO 2 | + | + |
| *P. rettgeri* | NCTC 7475 | + | + |
| *Providencia stuartii* | PST 1 | + | + |
| *Providencia stuartii* | PST 2 | + | + |
| *Providencia alcalifaciens* | PAL 1 | + | + |
| *Providencia alcalifaciens* | PAL 2 | + | – |
| *P. mirabilis* | NCTC 10975 | – | – |
| *P. mirabilis* | PMI 1 | – | – |
| *P. mirabilis* | PMI 2 | – | – |
| *P. vulgaris* | PVU 4 | – | – |
| *P. vulgaris* | PVU 2 | – | – |
| *P. vulgaris* | PVU 5 | – | – |
| *P. penneri* | PPE 1 | – | – |
| *Vibrio parahaemolyticus* | NCTC 12205 | – | – |
| *Vibrio parahaemolyticus* | NCTC 11344 | – | – |
| *Vibrio furnissii* | NCTC 11218 | – | – |
| *Vibrio hollisae* | NCTC 11640 | – | – |
| *Vibrio cholera* | NCTC 12945 | – | – |
| *Vibrio cholera* | NCTC 10732 | – | – |
| *Vibrio cholera* | NCTC 7270 | – | – |
| *Vibrio cholera* | NCTC 6585 | – | – |
| *Vibrio cholera* | NCTC 8021 | – | – |
| *Vibrio parahaemolyticus* | NCTC 10903 | – | – |
| *Vibrio cincinnatiensis* | NCTC 12012 | + | – |
| *Vibrio parahaemolyticus* | NCTC 10441 | – | – |

TABLE 1-continued

Hydrolysis of glycosides of 3'4'-dihydroxyflavone
by Gram negative bacteria.

| Strain | Reference No. | β-Glucoside | β-Riboside |
|---|---|---|---|
| Vibrio harveyi | NCTC 11346 | + | ++ |
| Vibrio vulnificus | NCTC 11067 | + | − |
| Vibrio metschnikovii | NCTC 8443 | − | ++ |
| Vibrio cholerae | NCTC 8042 | − | − |
| Vibrio cholerae | NCTC 10255 | − | − |
| Vibrio cholerae | NCTC 10954 | − | − |
| Vibrio mimicus | NCTC 11435 | − | − |
| Vibrio anguillarum | NCTC 12159 | − | − |
| Vibrio vulnificus | NCTC 11066 | + | − |
| Vibrio fluvialis | NCTC 11327 | ++ | ++ |
| Vibrio parahaemolyticus | NCTC 10884 | − | − |
| Vibrio cholerae | NCTC 7254 | − | − |
| Vibrio alcaligenes | NCTC 12160 | − | − |

Abbreviations:
NCTC National Collection of Type Cultures (UK)
ATCC American Type Culture Colllection.
Key
+ Positive reaction with the substrate
++ Strong positive reaction with the substrate
− No detectable reaction
−* indicates expected positive reaction as determined using indoxyl glucosides.

TABLE 2

Hydrolysis of 3'4'-dihydroxyflavone-β-glucoside and
3'4'-dihydroxyflavone-β-riboside by Gram positive organisms

| Strain | Reference No. | Glucoside | Riboside |
|---|---|---|---|
| Streptococcus oralis | NCTC11427 | − | − |
| Streptococcus sanguis | NCTC 7863 | − | − |
| Streptococcus constellatus | NCTC 11325 | − | − |
| Streptococcus mitis | NCTC 12261 | − | − |
| Streptococcus salivarius | NCTC 8618 | ++ | − |
| Streptococcus crista | NCTC 12479 | − | − |
| Streptococcus vestibularis | NCTC 12166 | − | − |
| Streptococcus gordonii | NCTC 7865 | − | − |
| Streptococcus pneumoniae | NCTC 7465 | − | − |
| Streptococcus agalactiae | NCTC 8181 | − | − |
| Streptococcus milleri | wild | − | − |
| Haemolytic streptococcus A | 1 | − | − |
| Haemolytic streptococcus A | 2 | − | − |
| Haemolytic streptococcus A | 3 | − | − |
| Haemolytic streptococcus B | 1 | − | − |
| Haemolytic streptococcus B | 2 | − | − |
| Haemolytic streptococcus B | 3 | − | − |
| Haemolytic streptococcus C | 1 | − | − |
| Haemolytic streptococcus C | 67736 | − | − |
| Haemolytic streptococcus C | 68350 | − | − |
| Haemolytic streptococcus G | 1 | − | − |
| Haemolytic streptococcus G | 2 | − | − |
| Haemolytic streptococcus G | 3 | − | + |
| Listeria seerigeri | PHLS wild | ++ | − |
| Listeria innocua | PHLS wild | ++ | − |
| Listeria ivanovii | PHLS wild | ++ | + |
| Arcanobacterium haemolyticus | NCTC 52 | − | + |
| Bacillus licusniforms | NCIMB 9375 | + | − |
| Bacillus cereus | NCTC | + | − |
| Corynebacterium diphtheria | NEQAS | − | ++ |
| C. diphtheriae | NCTC 10356 | − | ++ |
| C. diphtheriae | NCTC 11397 | − | ++ |
| C. diphtheriae | NCTC 3987 | − | + |
| Staphylococcus aureus | 1 | − | ++ |
| Staphylococcus aureus | 2 | − | ++ |
| Staphylococcus aureus | 3 | − | ++ |
| Staphylococcus aureus | 4 | − | ++ |
| Staphylococcus aureus | 5 | − | ++ |
| Staphylococcus haemolyticus | RB 66 | − | + |
| Staphylococcus haemolyticus | RB 67 | − | + |
| Staphylococcus haemolyticus | RB 68 | − | + |
| Staphylococcus haemolyticus | RB 69 | − | + |
| Staphylococcus haemolyticus | RB 70 | − | + |
| Staphylococcus epidermidis | RB60 | − | ++ |
| Staphylococcus epidermidis | RB62 | − | + |
| Staphylococcus epidermidis | RB63 | − | + |
| Staphylococcus epidermidis | RB64 | ++ | + |
| Staphylococcus epidermidis | RB65 | − | + |
| Staphylococcus saprophyticus | 1 | − | ++ |
| Staphylococcus saprophyticus | 2 | − | ++ |
| Staphylococcus saprophyticus | 3 | − | ++ |
| Staphylococcus saprophyticus | 4 | − | ++ |
| Staphylococcus saprophyticus | 5 | − | ++ |
| Enterococcus raffinosis | NCTC 13192 | ++ | + |
| Enterococcus mundtii | NCTC 12363 | ++ | + |
| Enterococcus durans | NCTC 8307 | ++ | − |
| Enterococcus gellinarum | NCTC 11428 | ++ | + |
| Enterococcus faecium | 121285 - wild '99 | ++ | − |
| Enterococcus casseflavus | NCTC 12361 | ++ | − |
| Enterococcus faecalis | 1 | ++ | − |
| Enterococcus faecalis | 2 | ++ | + |
| Enterococcus faecalis | 3 | ++ | + |
| Enterococcus faecalis | 4 | ++ | + |
| Enterococcus faecalis | 5 | ++ | + |
| Enterococcus faecalis | 6 | ++ | + |
| Enterococcus faecalis | 7 | ++ | − |
| Enterococcus faecium | 1 | ++ | − |
| Enterococcus faecium | 2 | ++ | − |
| Enterococcus faecium | 3 | ++ | − |
| Enterococcus faecium | 4 | ++ | + |
| Enterococcus faecium | 5 | ++ | − |
| Enterococcus faecium | 6 | ++ | + |
| Enterococcus faecium | 7 | ++ | − |
| NEGATIVE CONTROL | | − | − |

Key
+ Positive reaction with the substrate
++ Strong positive reaction with the substrate
− No detectable reaction
−* Indicates expected positive reaction as determined using indoxylic glucosides.

EXAMPLE 3

3',4'-Dihydroxyflavone-4'-β-galactopyranoside sodium salt

Sodium hydroxide (0.08 g) was dissolved in deionised water (2.33 g) and the resulting solution was cooled to 4° C. in a refrigerator. Meanwhile, 3',4'-dihydroxyflavone (0.5 g), acetobromogalactose (0.918 g) and acetone (5.57 ml) were added to a 25 ml round bottomed flask equipped with a magnetic stirrer and stirred for 5 mins. The cooled sodium hydroxide solution was added to the suspension of 3,'4'-dihydroxyflavone and the mixture changed from a yellow/brown suspension into a deep-red/brown solution. After stirring at room temperature for 5-10 mins., the reaction mixture had become an orange/brown suspension. Stirring was continued overnight at ambient temperature. The precipitated 3',4'-dihydroxyflavone was filtered off, washing through with acetone (5-10 ml) and the filtrate was evaporated down using a rotary evaporator to form two distinct phases. The top layer (aqueous) was discarded and the lower layers triturated with dichloromethane (2 ml) thereby precipitating unreacted 3',4'-dihydroxyflavone. After filtering off the precipitate, the dichloromethane solution was washed with a saturated sodium bicarbonate solution (3×10 ml) then deionised water (5 ml). The dichloromethane layer was separated from the water layer, dried (magnesium sulfate) and stripped to dryness to give 311 mg of the product acetate. Methanol was added to the acetate (310 mg) and all dissolved. The solution was basified by the addition of a saturated sodium methoxide solution in methanol. At pH9, a thick precipitate formed and the mixture was basified further to pH 10-11 then left overnight. The product was filtered off, washing with acetone (approx. 10 ml). Yield, 80 mg (red/brown solid).

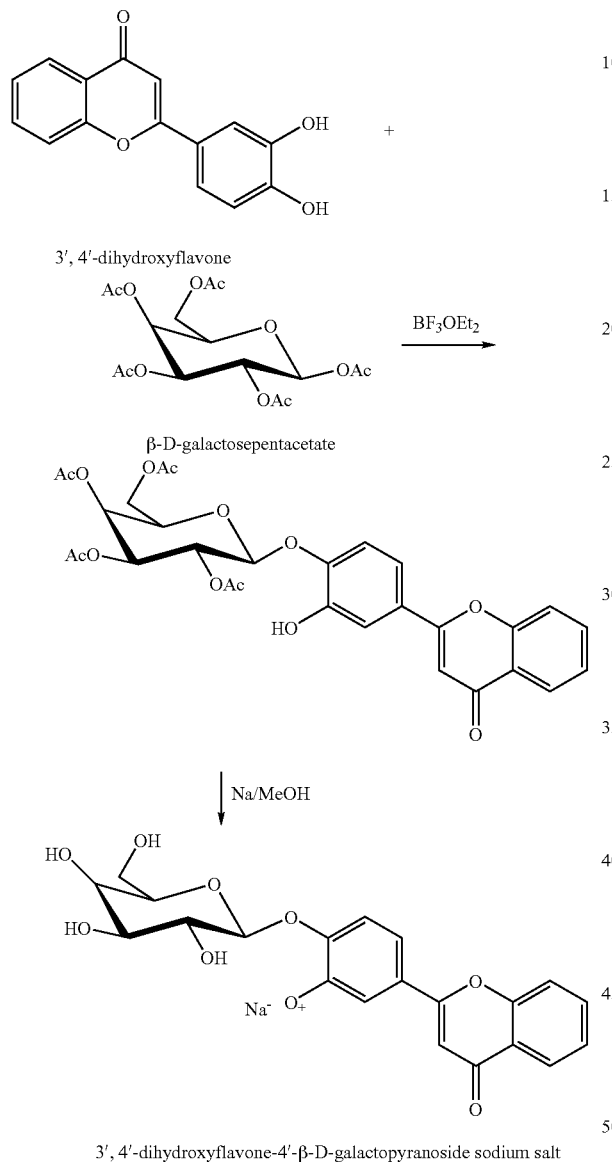

3', 4'-dihydroxyflavone-4'-β-D-galactopyranoside sodium salt

EXAMPLE 4

3',4'-Dihdroxyflavone-4'-phosphate

3',4'-Dihydroxyflavone (127 mg) was suspended in acetonitrile (15 ml) in a 50 ml round bottomed flask with nitrogen inlet and side arm. After flushing with nitrogen for 10 mins the suspension was cooled to −10° C. and carbon tetrachloride (0.26 ml), diisopropylethylamine (0.2 ml) and dimethylaminopyridine (6 mg) were added via the side arm. After stirring for 1 min, dibenzylphosphite (290 mg) was added dropwise. After 1 h, a mixture composed of a solution of potassium dihydrogen phosphate (0.5 moles) in water (3 ml) and acetonitrile (20 ml) was added and the solution extracted with ethyl acetate (3×25 ml). After drying over magnesium sulphate the solution was filtered and the filtrate concentrated in vacuo. The orange oil so obtained was dissolved in methanol (15 ml) and 10% palladium on charcoal catalyst (25 mg) was added. After flushing with nitrogen the benzyl groups were removed by passing hydrogen through the solution for 1 h at atmospheric pressure. The solution was then filtered and the methanol removed by evaporation. The residue was then partitioned between chloroform (50 ml) and water (50 ml). After separation from the organic layer the aqueous layer was washed with further portions of chloroform (2×50 ml) before being evaporated to dryness. Trituration with the minimum amount of diethyl ether afforded the product as a solid (87 mg).

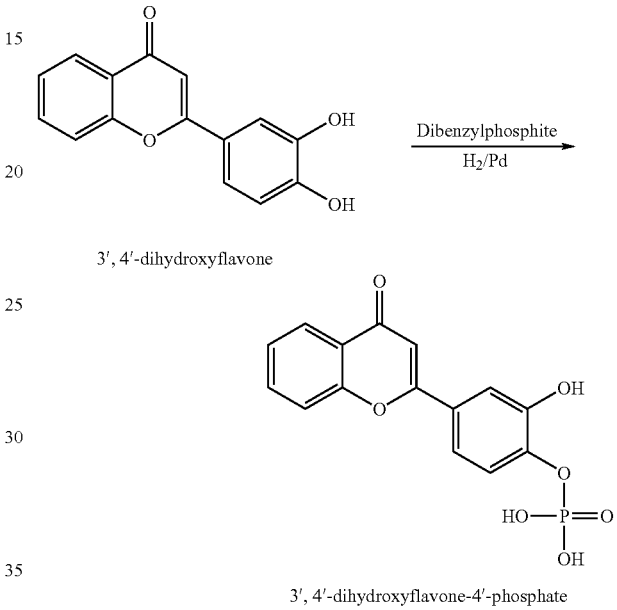

3', 4'-dihydroxyflavone-4'-phosphate

EXAMPLE 5

Synthesis of Catechol-β-D-ribofuranoside sodium salt (2-hydroxyphenyl-β-D-ribofuranoside sodium salt)

A 500 ml round bottomed flask equipped with a magnetic stirrer was charged with catechol (33 g), 3 Å molecular sieves (20 g), and dichloromethane (200 ml). The solution which formed was stirred for 10 minutes, then boron trifluoride diethyl etherate (10 ml) was added in one portion. After 1 hour the reaction mixture was filtered, then it was washed in a separating funnel sequentially with equal volumes of saturated sodium bicarbonate (five times) and de-ionised water (twice), then dried over magnesium sulfate. Removal of the drying agent and evaporation afforded a pale yellow oil that slowly solidified. The solid was dissolved in hot industrial methylated spirits (IMS) (50 ml) and then stored at 4° C. for 16 hours to allow crystallisation to complete. The white solid was collected by vacuum filtration and washed with IMS (20 ml) in two portions. After one day drying in air the yield of protected riboside was 17.1 g. The protected riboside (15 g) was suspended in methanol (150 ml) and a solution made up of sodium (2 g) in methanol (50 ml) was added to it. Initially the solid dissolved but this was soon replaced by a heavy precipitate. The reaction mixture was set aside for 16 hours. The solid was then collected by vacuum filtration and washed with methanol (5 ml). The hygroscopic solid was then immediately transferred to a desiccator and dried under vacuum over phosphorous pentoxide for 6 hours. The yield of white powder was 4.3 g.

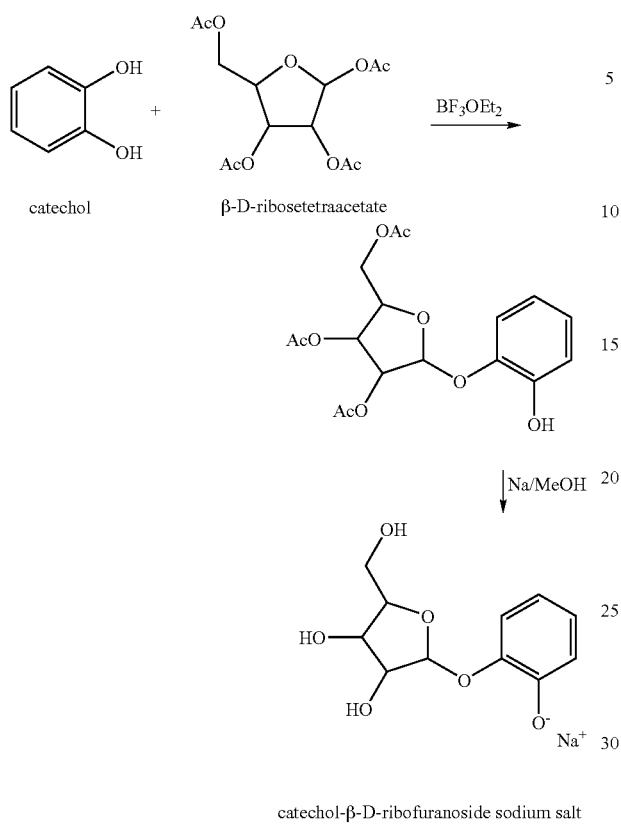

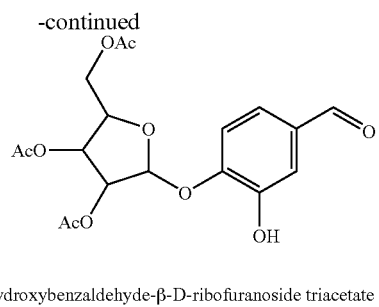

3, 4-dihydroxybenzaldehyde-β-D-ribofuranoside triacetate

EXAMPLE 7

Synthesis of 3,4-Dihydroxybenzaldehyde-4-β-D-ribofuranoside sodium salt

To a mixture of 3,4-dihydroxybenzaldehyde-4-β-D-ribofuranoside triacetate (5.0 g) produced as in Example 6 in methanol was added a solution of sodium (0.5 g) in methanol. The triacetate dissolved and was replaced by a dense precipitate. After 5 hours this was filtered off under vacuum and washed on the filter with methanol (5 ml) and diethyl ether (10 ml). Drying for 4 hours under vacuum over phosphorous pentoxide gave the product as a pale cream solid (3.1 g).

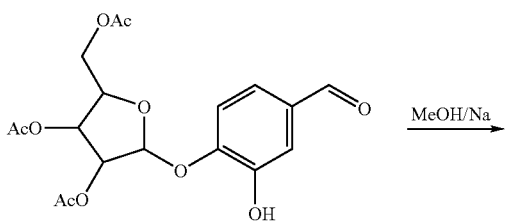

3, 4-dihydroxybenzaldehyde-β-D-ribofuranoside triacetate

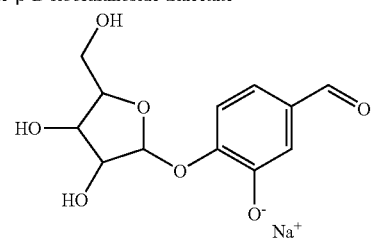

3, 4-dihydroxybenzaldehyde-β-D-ribofuranoside sodium salt

EXAMPLE 6

Synthesis of 3,4-Dihydroxybenzaldehyde-4-β-D-ribofuranoside triacetate

To a 3 L round bottomed flask provided with a magnetic stirrer was added 3,4-dihydroxybenzaldehyde (50 g), β-D-ribose tetraacetate (47 g), 3 Å molecular sieves (350 g) and dichloromethane (1.4 L). After stirring this mixture for 5 minutes boron trifluoride diethyl etherate (75 ml) was added in one lot and stirring was then continued for a further 20 minutes whereupon the molecular sieves were removed by filtration. The filtrate was washed with an equal volume of saturated sodium bicarbonate four times, dried over magnesium sulfate for 1 hour then evaporated to dryness. The residual pale yellow solid was dissolved in hot IMS (70 ml), and stored at 4° C. for 6 hours. The product was harvested by filtration. Drying over phosphorous pentoxide under vacuum afforded 12.4 g of an off-white solid.

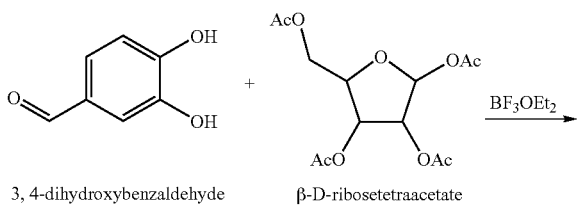

3, 4-dihydroxybenzaldehyde     β-D-ribosetetraacetate

EXAMPLE 8

Synthesis of 3,4-Dihydroxybenzaldehydesemicarbazone-4-β-D-ribofuranoside

To a solution of 3,4-dihydroxybenzaldehyde-4-β-D-ribofuranoside sodium salt (0.5 g) produced as in Example 7 in de-ionised water (5 ml) was added a solution of semicarbazide hydrochloride (1 g) and potassium acetate (1.5 g) in water (5 ml). The mixture was heated in a boiling water bath for 10 minutes then allowed to cool. After concentrating the solution to half its original volume by evaporation the product crystallised out. It was collected by vacuum filtration and, after washing with water (2 ml), it was dried in a desiccator in vacuo over phosphorous pentoxide. The product was a white solid (300 mg).

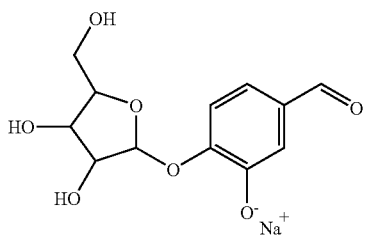 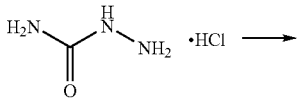

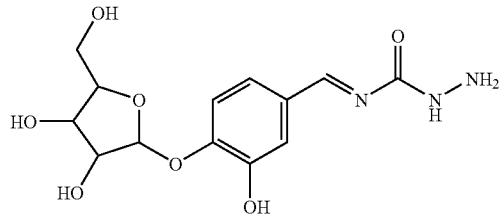

3,4-dihydroxybenzaldehyde-β-D-ribofuranoside sodium salt    semicarbazide hydrochloride 3,4-dihydroxybenzaldehydesemicarbazone-β-D-ribofuranoside

EXAMPLE 9

Synthesis of 3,4-Dihydroxychalcone-4-β-D-ribofuranoside

To a solution of 3,4-dihydroxybenzaldehyde-4-β-D-ribofuranoside sodium salt (0.25 g) produced as in Example 7 in IMS was added sodium hydroxide (0.1 g) in de-ionised water (3 ml) and acetophenone (0.1 g). The mixture was stirred at room temperature for 9 days after which time the reaction was evaporated to dryness. The product was obtained as a red solid.

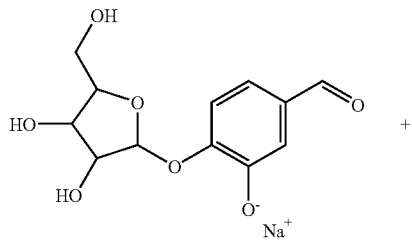

3,4-dihydroxybenzaldehyde-β-D-ribofuranoside sodium salt

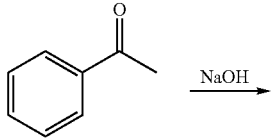

acetophenone

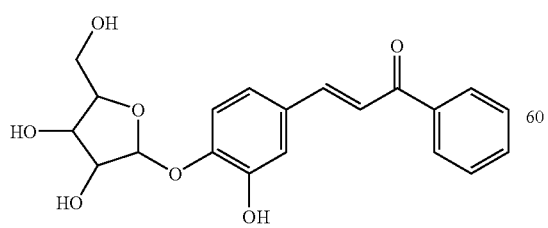

3,4-dihydroxychalcone-β-D-ribofuranoside

EXAMPLE 10

Synthesis of 3',4'-Dihydroxyaurone-4'-β-D-ribofuranoside

To a mixture of 3,4-dihydroxybenzaldehyde-4-β-D-ribofuranoside triacetate (0.4 g) produced as in Example 6 and 3-coumaranone (0.17 g) in IMS (20 ml) was added a solution of IMS saturated with hydrogen chloride gas (0.05 ml). The mixture was stirred at room temperature for 3 days and then evaporated to dryness. The resulting solid was dissolved in methanol (2 ml) and a solution of sodium (50 mg) in methanol (0.5 ml) was added giving a blood-red solution. This solution was evaporated to dryness and partitioned between de-ionised water is (25 ml) and dichloromethane (50 ml). The aqueous layer was extracted with two further dichloromethane washes (50 ml) before being evaporated to dryness. The product was obtained as a red solid.

-continued

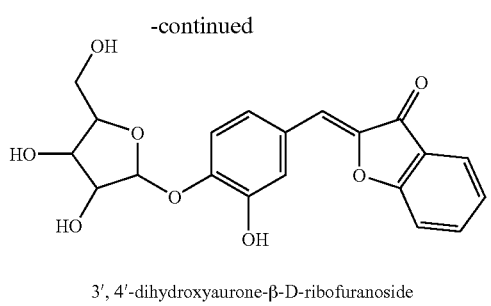

3′, 4′-dihydroxyaurone-β-D-ribofuranoside

EXAMPLE 11

Synthesis and Evaluation of 3',4'-dihydroxy-3-methoxyflavone 4' Phosphate

3',4'-Dihydroxy-3-methoxyflavone (F. A. A. van Acker et al., *J. Med. Chem.,* 43, 3752-3760, (2000)), (143 mg) was suspended in acetonitrile (15 ml) in a 50 ml round bottomed flask with nitrogen inlet and side arm. After flushing with nitrogen for 10 mins the suspension was cooled to −10 degrees C. and carbon tetrachloride (0.26 ml), diisopropylethylamine (0.2 ml) and dimethylaminopyridine (6 mg) were added via the side arm. After stirring for 1 min, dibenzylphosphite (152 mg) was added drop wise. After 1 h, a mixture composed of a solution of potassium dihydrogen phosphate (0.5 moles) in water (3 ml) and acetonitrile (20 ml) was added and the solution extracted with ethyl acetate (3×25 ml). After drying over magnesium sulphate the solution was filtered and the filtrate concentrated in vacuo. The orange oil so obtained was dissolved in methanol (20 ml) and 10% palladium on charcoal. catalyst (30 mg) was added. After flushing with nitrogen the benzyl groups were removed by passing hydrogen through the solution for 1 h at atmospheric pressure. The solution was then filtered and the methanol removed by evaporation. The residue was then partitioned between chloroform (50 ml) and water (50 ml). After separation from the organic layer the aqueous layer was washed with further portions of chloroform (2×50 ml) before being evaporated to dryness. Trituration with the minimum amount of acetone afforded the product as a solid (90 mg).

When evaluated the same method was used as in Example 1 and *C. perfringens* was incubated anaerobically, the background colour of the agar was olive green and organisms showing enzyme activity produced dark green colonies. There was no colour diffusion from the colonies. All species tested grew well on this medium. The results are shown in table 3 below.

TABLE 3

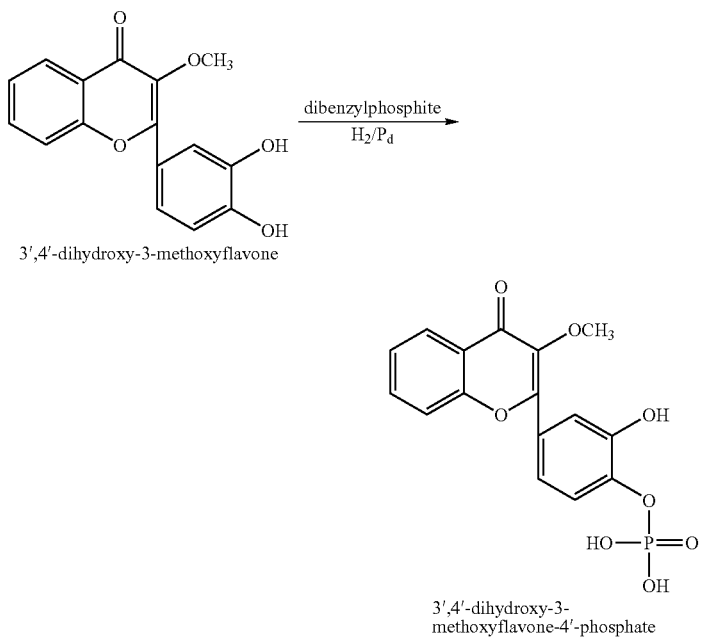

3′,4′-dihydroxy-3-methoxyflavone

3′,4′-dihydroxy-3-methoxyflavone-4′-phosphate

| Strain | ref number | colony appearance | Interpretation |
|---|---|---|---|
| *Acinetobacter lwoffii* | ATCC 15309 | colourless | Negative |
| *Yersinia enterocolitica* | NCTC 11197 | colourless | Negative |
| *Clostridium perfringens* | NCTC 8181 | dark green | Positive |
| *Staphylococcus aureus* | NCTC 6571 | dark green | Positive |
| *Escherichia coli* | NCTC 10418 | pale green | Positive |
| *Enterococcus faecalis* | NCTC 775 | small dark green/black | Positive |

EXAMPLE 12

3',4'-dihydroxy-3-methoxyflavone-4'-β-D-galactopyranoside

The compound shown in the title is synthesised from 3',4'-dihydroxy-3-methoxyflavone (as used in Example 11) by a method analogous to Example 3. The compound was evaluated by the method described in Example 1 with *K. pneumoniae*, in the presence of a range of different metal salts. The metal salts were all included in the medium at a concentration of 500 mg/l. The medium further included isopropyl-D-thiogalactopyranoside (IPTG) at a concentration of 30 mg/l. Table 4 indicates the colour of the colonies formed.

TABLE 4

Evaluation of 3',4'-dihydroxy-3-methoxyflavone-4'-β-D-galactoside with metal salts forming chelates

| Metal | Colour of *K. pneumoniae* colonies |
|---|---|
| Zn | No growth |
| Co | No growth |
| Mn | Pale orange |
| Sn | Yellow |
| Ba | Yellow |
| Al | Yellow |
| Sr | Yellow |
| Bi | Rusty orange |
| Fe | Brown |
| No metal | Diffuse yellow |

EXAMPLE 13

3'4'-dihydroxyflavone-4'-β-D-galactopyranoside with different Metal Salts

The compound of the title, synthesised as described in Example 3, was evaluated by the method described in Example 1, in the presence of a range of metal salts, with an inoculum of *K. pneumoniae*. The metal salts were used at a concentration (as salt) of 500 mg/l and the medium also contained 30 mg/l IPTG. The cultures formed coloured colonies as indicated in table 5.

TABLE 5

| Metal | Colour of colonies |
|---|---|
| Zn | (inhibits; no growth) |
| Co | (inhibits; no growth) |
| Mn | Pale orange |
| Cu | Orange/brown |
| Sn | Pale yellow |
| Ba | Pale yellow |
| Al | Yellow |
| Sr | Yellow |
| Bi | Rusty orange |
| Fe | Dark brown or black |
| No metal | Diffuse pale yellow |

EXAMPLE 14

3',4'-dihydroxy-3-methoxyflavone-4'-β-D-ribofuranoside

The substrate shown in the heading was synthesised from the same flavone starting material as Example 11 by a method analogous to that of Example 2. The substrate was evaluated by the same method as described in Example 1 in the presence of metal salts. The species tested was *E. coli*. The precipitates were coloured almost identically to the corresponding products referred to in Table 4. When the aluminium salt-containing medium was used with a mixed culture of *E. coli* and *Yersinia entermcolitica*, the *E. coli* colonies were bright yellow and stood out very clearly. There was substantially no diffusion into the *Y. enterocolitica* colonies (negative for this substrate, thus colourless) even when the colonies were almost coincident.

EXAMPLE 15

3,4-dihydroxy-2-methoxybenzophenone-4-β-D-glucopyranoside

The title compound was synthesised from 3,4-dihydroxy-2-methoxybenzophenone and acetobromoglucose by a method analogous to Example 3. It was obtained as a pale yellow powder. 3,4-Dihydroxy-2-methoxybenzophenone was made in the following way. To a solution of sodium tetraborate (16 g) in water (200 ml) was added 2,3,4-trihydroxybenzophenone (4.6 g). To the stirred suspension was added a solution of potassium hydroxide (4.5 g) in water (20 ml) to give a solution at approximately pH13. Dimethyl sulphate (10 ml) was added dropwise over 2 hours whilst maintaining the pH at 12-13 with more potassium hydroxide solution as required. After leaving for one day at 5° C. the solution was acidified to pH3 by the addition of 4M hydrochloric acid to produce a yellow precipitate. This solid was collected by suction filtration, washed with water and dried. Recrystallisation from boiling ethanol gave 3,4-dihydroxy-2-methoxybenzophenone as fine yellow crystals.

The compound was evaluated on a screen of selected Gram negative bacteria using the method described in Example 1, in the presence of ferric ammonium nitrate at 500 mg/l. The results are shown in table 6. The background agar was beige. The colonies which were coloured showed little diffusion. When tested with Gram positive organisms the compound seemed to be growth inhibiting.

TABLE 6

| Organism tested | colony colour | growth |
|---|---|---|
| *E. coli* | cream | ++ |
| *S. sonnei* | cream | ++ |
| *E. faecalis* | cream | Tr |
| *L. monocytogenes* | pale black | Tr |
| *K. pneumoniae* | red/brown | ++ |
| *S. aureus* | cream | ++ |

Key:
++ strong growth
Tr trace growth

EXAMPLE 16

Mixed Substrates

Two growth media were produced one of which contained a mixture of substrates one being in accordance with the present invention and the other of which contained just the other substrate. The media were evaluated using six bacterial strains. The results are shown in Table 7. Synthesis of X-β-D-ribofuranoside is disclosed in copending PCT based on GB 0221716.4.

| Medium A (components per liter) | |
| --- | --- |
| Columbia agar (Oxoid) | 40 g |
| 5-Bromo-4-chloro-3-indolyl β-D-ribofuranoside (also known as X-β-D-ribofuranoside) | 80 mg |
| 6-chloro-3-indolyl β-D-glucopyranoside | 200 mg |
| Medium B (components per liter) | |
| Columbia agar (Oxoid) | 40 g |
| 3'4'-dihydroxyflavone-4'-β-D-ribofuranoside | 300 mg |
| 6-chloro-3-indolyl β-D-glucopyranoside | 200 mg |
| Ferric ammonium citrate | 500 mg |

| | A | B |
| --- | --- | --- |
| *Enterobacter cloacae* NCTC 11936 | Purple | Black |
| *Eschenchia coli* NCTC 10418 | Green | Black |
| *Klebsiella pneumoniae* NCTC 10896 | Purple | Black |
| *Salmonella typhimurium* NCTC 74 | Green | Black |
| *Serratia marcescens* NCTC 10211 | Purple | Black |
| *Yersinia enterocolitica* NCTC 11176 | Colourless | Colourless |

The reference example using medium A shows that the rose glucoside (also used in the medium of the invention, medium B) is hydrolysed by some of the species of bacteria, and that some of the species are positive for β-D-ribofuranosidase. Medium B shows that the product of the cleavage of the compound of the present invention in the presence of iron masks the cleavage product by forming a black precipitate. This ability to mask may be of utility for some applications.

The invention claimed is:

1. A chromogenic enzyme substrate of the formula I

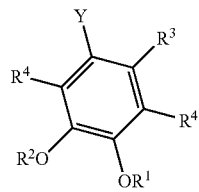

in which $R^1$ is an enzyme cleavable group selected from the group consisting of β-D-galactopyranosyl, α-D-galactopyranosyl, decanoyl, octanoyl, inositol-1-phosphatyl, phosphatyl, β-D-ribofuranosyl, α-L-arabinopyranosyl, butyryl, nonanoyl, palmitoyl, lignoceroyl, α-L-fucopyranosyl, β-L-fucopyranosyl, α-D-fucopyranosyl, β-D-fucopyranosyl, α-D-mannopyranosyl, β-D-mannopyranosyl, oleoyl, sulphatyl, α-D-xylopyranosyl and β-D-xylopyranosyl;

$R^2$ is hydrogen;

Y has the structure of VII or VIII

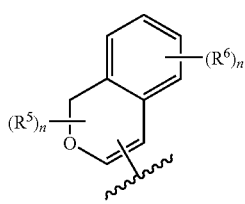

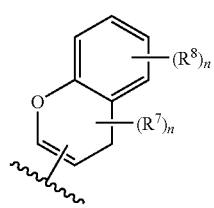

wherein each of $R^5$, $R^6$, $R^7$ and $R^8$ is selected from the group consisting of hydroxyl, $C_{1-24}$ alkyl, $C_{2-12}$ alkenyl, $C_{1-4}$ alkoxy, acyl, halogen, nitro, aryl and acyloxy groups, in which alkyl and aryl groups which are substituents may be substituted by amino, hydroxyl, peptide, acyloxy, alkoxy and aryl groups or two group $R^5$ and $R^7$ on the same carbon are=O;

n is 0, 1 or 2;

$R^3$ and $R^4$ are selected from the group consisting of H, $C_1$ to $C_6$-alkyl, -alkoxy and hydroxyalkyl, halogeno, nitro, acyl, acyloxy, aralkyl, aryl and amido groups, wherein $R^3$ and $R^4$ are not linked to form a fused ring;

or a salt or hydrate of such a compound.

2. A kit of components for use in the detection of enzyme activity on a solid medium wherein said components include;

a) an enzyme substrate, that is a compound of the formula I, II, III or IV:

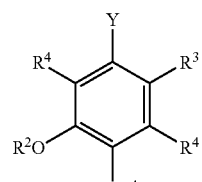

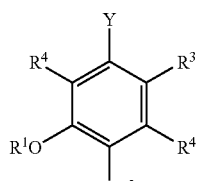

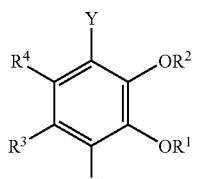

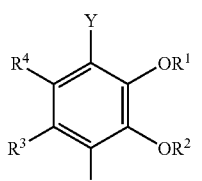

where $R^1$ and $R^2$ are H or an enzymically cleavable group;

$R^1$ and $R^2$ cannot both be H;

Y has the structure of VII or VIII

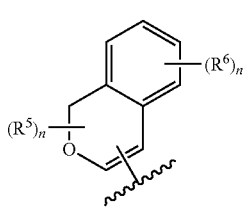

-continued

VIII

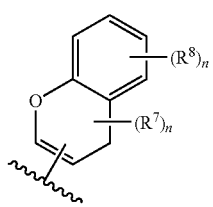

wherein each of $R^5$, $R^6$, $R^7$ and $R^8$ is selected from the group consisting of hydroxyl, $C_{1-24}$ alkyl, $C_{2-12}$ alkenyl, $C_{1-4}$ alkoxy, acyl, halogen, nitro, aryl and acyloxy groups, in which alkyl and aryl groups which are substituents may be substituted by amino, hydroxyl, peptide, acyloxy, alkoxy and aryl groups or two groups $R^5$ and $R^7$ on the same carbon are =O;

n is 0, 1 or 2;

$R^3$ and $R^4$ are selected from the group consisting of H, $C_1$ to $C_6$-alkyl, -alkoxy and hydroxyalkyl, halogeno, nitro, acyl, acyloxy, aralkyl, aryl and amido groups, wherein $R^3$ and $R^4$ are not linked to form a fused ring;

or a salt or hydrogen of such a compound; and b) a metal ion compound which is chelatable by the compound which is formed from the cleaved chromogenic portion;

wherein said components comprise a solid medium which supports the growth of microbes, the said substrate and the said metal ion.

3. A kit according to claim 2 in which the said components are ready mixed or are in separate containers.

4. A kit according to claim 2, in which the metal salt is a salt of iron, aluminium or bismuth.

5. A kit of components for use in the detection of enzyme activity on a solid medium wherein said components include;

a) an enzyme substrate, that is a compound of the formula I:

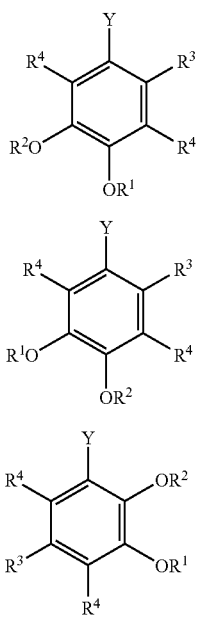

-continued

IV

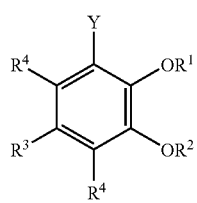

where $R^1$ is an enzymically cleavable group group selected from the group consisting of β-D-glucuronyl, β-D-galactopyranosyl, α-D-galactopyranosyl, decanoyl, octanoyl, inositol- 1-phosphatyl, phosphatyl, β-D-ribofuranosyl, α-L-arabinopyranosyl, butyryl, nonanoyl, palmitoyl, lignoceroyl, α-L-fucopyranosyl, β-L-fucopyranosyl, α-D-fucopyranosyl, β-D-fucopyranosyl, α-D-mannopyranosyl, β-D-mannopyranosyl, oleoyl, sulphatyl, α-D-xylopyranosyl and β-D-xylopyranosyl;

$R^2$, $R^3$ and $R^4$ are H;

and Y has the structural formula IX

IX

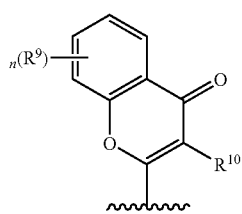

n is 0, $R^{10}$ is H or a salt or hydrate of such a compound; and b) a metal ion compound which is chelatable by the compound which is formed from the cleaved chromogenic portion.

6. A kit according to claim 5, in which the said components are ready mixed or are in separate containers; wherein said components comprise a solid medium which supports the growth of microbes, the said substrate and the said metal ion; and in which the metal salt is a salt of iron, aluminium or bismuth.

7. A chromogenic enzyme substrate according to claim 1 wherein R2, R3 and R4 are H, and Y has the structural formula IX

IX

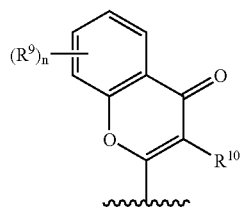

n is 0, $R^{10}$ is H and $R^1$ is selected from the group consisting of β-D-galactopyranosyl, α-D-galactopyranosyl, decanoyl, octanoyl, inositol-1-phosphatyl, phosphatyl, β-D-ribofuranosyl, α-L-arabinopyranosyl, butyryl, nonanoyl, palmitoyl, lignoceroyl, α-L-fucopyranosyl, β-L-fucopyranosyl, α-D-fucopyranosyl, β-D-fucopyranosyl, α-D-mannopyranosyl, β-D-mannopyranosyl, oleoyl, sulphatyl, α-D-xylopyranosyl and β-D-xylopyranosyl.

* * * * *

UNITED STATES PATENT AND TRADEMARK OFFICE
CERTIFICATE OF CORRECTION

PATENT NO. : 7,531,646 B2 Page 1 of 1
APPLICATION NO. : 10/493482
DATED : May 12, 2009
INVENTOR(S) : M. Burton It is certified that error appears in the above-identified patent and that said Letters Patent is hereby corrected as shown below:

Title Page Item (54), please delete the title as it appears and insert the correct title

--CHROMOGENIC ENZYME SUBSTRATES AND KITS CONTAINING THEM--

Signed and Sealed this

Fourth Day of August, 2009

JOHN DOLL
*Acting Director of the United States Patent and Trademark Office*

UNITED STATES PATENT AND TRADEMARK OFFICE
CERTIFICATE OF CORRECTION

| | |
|---|---|
| PATENT NO. | : 7,531,646 B2 |
| APPLICATION NO. | : 10/493482 |
| DATED | : May 12, 2009 |
| INVENTOR(S) | : M. Burton |

It is certified that error appears in the above-identified patent and that said Letters Patent is hereby corrected as shown below:

Title Page Item (54) and Column 1, lines 1 and 2, please delete the title as it appears and insert the correct title

--CHROMOGENIC ENZYME SUBSTRATES AND KITS CONTAINING THEM--

This certificate supersedes the Certificate of Correction issued August 4, 2009.

Signed and Sealed this

First Day of September, 2009

David J. Kappos
*Director of the United States Patent and Trademark Office*